United States Patent
Smith et al.

(10) Patent No.: US 7,071,207 B2
(45) Date of Patent: Jul. 4, 2006

(54) PREPARATION AND USE OF 1,5,6,7-TETRAHYDROPYRROLO [3,2-C]PYRIDINE DERIVATIVES FOR TREATMENT OF OBESITY

(75) Inventors: Roger A. Smith, Madison, CT (US); Stephen J. O'Connor, Guilford, CT (US); Wai C. Wong, Trumbull, CT (US); Soongyu Choi, Skillman, NJ (US); Harold C. Kluender, Trumbull, CT (US); Jianmei Fan, Hamden, CT (US); Zhonghua Zhang, Derby, CT (US); Rico C. Lavoie, Chesire, CT (US); Brent L. Podlogar, Flemington, NJ (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 216 days.

(21) Appl. No.: 10/487,976

(22) PCT Filed: Sep. 24, 2002

(86) PCT No.: PCT/US02/30541

§ 371 (c)(1),
(2), (4) Date: Feb. 27, 2004

(87) PCT Pub. No.: WO03/027114

PCT Pub. Date: Apr. 3, 2003

(65) Prior Publication Data

US 2004/0224970 A1    Nov. 11, 2004

Related U.S. Application Data

(60) Provisional application No. 60/324,443, filed on Sep. 24, 2001.

(51) Int. Cl.
| | |
|---|---|
| *A61K 31/40* | (2006.01) |
| *A61K 31/395* | (2006.01) |
| *A61K 31/437* | (2006.01) |
| *C07D 471/04* | (2006.01) |
| *C07D 471/14* | (2006.01) |

(52) U.S. Cl. .................. 514/300; 514/318; 514/333; 546/113; 546/276.7; 546/289

(58) Field of Classification Search ............ 546/113, 546/289, 276.7; 514/300, 318, 333
See application file for complete search history.

(56) References Cited

U.S. PATENT DOCUMENTS

| 3,992,544 A | 11/1976 | Archibald et al. ......... 424/263 |
| 6,011,044 A * | 1/2000 | Choi et al. .................. 514/292 |
| 2002/0013336 A1 | 1/2002 | Peter et al. ................. 514/302 |

FOREIGN PATENT DOCUMENTS

| JP | EP-0725068 A1 * | 8/1996 |
| WO | 0043397 | 7/2000 |
| WO | 0101969 | 11/2001 |

OTHER PUBLICATIONS

Nagai, et al., Studies on Phsychotropic Agents. II.I Synthesis of 1-Substituted-3-(p-fluorophenacyl)piperidines and the Related Compounds, Chem. Pharm. Bull., 25, 1911-1922 (1977).
Nagarajan, et al., Antiimplantation Agents: Part III-1,2-Diaryl-4,5-polymethylenepyrroles & 1,2-Diaryl-4oxo- & 1,2-Diaryl-4-hydroxy-4,5,6,7-tetrahydroindoles, Indian Journal of Chemistry, 24B, 98-111 (1985).

* cited by examiner

*Primary Examiner*—Cecilia Tsang
*Assistant Examiner*—Lexington Hoffman
(74) *Attorney, Agent, or Firm*—Susan M. Pellegrino

(57) ABSTRACT

This invention relates to 1,5,6,7-tetrahydropyrrolo[3,2-c] pyridine derivatives which have been found to suppress appetite and induce weight loss. The invention also provides methods for synthesis of the compounds, pharmaceutical compositions comprising the compounds, and methods of using such compositions for inducing weight loss and treating obesity and obesity-related disorders.

27 Claims, No Drawings

PREPARATION AND USE OF 1,5,6,7-TETRAHYDROPYRROLO [3,2-C]PYRIDINE DERIVATIVES FOR TREATMENT OF OBESITY

This application is a 371 of PCT/US02/30541, filed on Sep. 24, 2002, which claims benefit of U.S. Provisional Application Ser. No. 60/324,443, filed Sep. 24, 2001.

FIELD OF THE INVENTION

This invention relates to the field of pharmaceuticals, in particular to the field of obesity treatment. More specifically, it relates to certain 1,5,6,7-tetrahydropyrrolo[3,2-c]pyridine compounds which are useful in the treatment of obesity and obesity-related disorders, and as weight-loss and weight-control agents.

BACKGROUND OF THE INVENTION

Obesity, which is defined as an excess of body fat relative to lean body mass, is a well-established risk factor for a number of potentially life-threatening diseases such as atherosclerosis, hypertension, diabetes, stroke, pulmonary embolism, sleep apnea, and cancer. Furthermore, it complicates numerous chronic conditions such as respiratory diseases, osteoarthritis, osteoporosis, gall bladder disease, and dyslipidemias. The enormity of this problem is best reflected in the fact that death rates escalate with increasing body weight. More than 50% of all-cause mortality is attributable to obesity-related conditions once the body mass index (BMI) exceeds 30 kg/m$^2$, as seen in 35 million Americans (Lee, JAMA 268:2045–2049, 1992). By contributing to greater than 300,000 deaths per year, obesity ranks second only to tobacco smoking as the most common cause of potentially preventable death (McGinnis, JAMA 270:2207–2212, 1993). Accompanying the devastating medical consequences of this problem is the severe financial burden placed on the health care system in the United States. It is estimated that 30–50% of the middle-age population may be considered as obese (Kuczmarski et al., JAMA 272:205–211, 1994). The economic impact of obesity and its associated illnesses from medical expenses and loss of income are reported to be in excess of $68 billion/a year (Colditz, Am. J. Clin. Nutr. 55:503S–507S, 1992). This figure does not include the greater than $30 billion per year spent on weight loss foods, products, and programs (Wolf, Pharmacoeconomics. 5:34–37, 1994).

The accumulation or maintenance of body fat bears a direct relationship to caloric intake. Comprehensive treatment programs, therefore, focused on behavior modifications to reduce caloric intake and increase physical activity using a myriad of systems. These methods have limited efficacy and are associated with recidivism rates exceeding 95% (NIH Technology Assessment Conference Panel, Ann. Intern. Med. 119:764–770, 1993).

Obesity has also been treated by administering specific agents, for example, anorectic agents, to obese subjects. However, anorectic agents such as dextroamphetamine, the combination of the non-amphetamine drugs phentermine and fenfluramine (Phen-Fen), and dexfenfluramine (Redux) alone, are associated with serious side effects. Indigestible materials such as olestra (OLEAN®, mineral oil or neopentyl esters (see U.S. Pat. No. 2,962,419)) have been proposed as substitutes for dietary fat. Garcinia acid and derivatives thereof have been described as treating obesity by interfering with fatty acid synthesis. Swellable crosslinked vinyl pyridine resins have been described as appetite suppressants via the mechanism of providing non-nutritive bulk (see, e.g., U.S. Pat. No. 2,923,662).

Surgical interventions, such as gastric partitioning procedures, jejunoileal bypass, and vagotomy, have also been developed to treat severe obesity (Greenway, Endo. Metab. Clin. N. Amer. 25:1005–1027, 1996). Although these surgical procedures are somewhat more effective in the long run, the acute risk benefit ratio has reserved these invasive procedures for morbidly obese patients according to the National Health Institutes (NIH) consensus conference on obesity surgery (BMI>40 kg/m$^2$) (NIH Conference, Ann. Intern. Med. 115:956–961, 1991). Therefore, this approach is not an alternative for the majority of overweight patients unless and until they become profoundly obese and are suffering the attendant complications.

Thus, new methods and compositions that promote weight-loss are urgently needed.

SUMMARY OF THE INVENTION

The present invention provides substituted 1,5,6,7-tetrahydropyrrolo[3,2-c]pyridine and substituted 1,5,6,7-tetrahydro-4H-pyrrolo[3,2-c]-pyridine-4-one derivatives which have been found to suppress appetite and induce weight loss in laboratory animals. The invention also provides methods for synthesis of the compounds, pharmaceutical compositions comprising the compounds, and methods of using such compositions for suppressing appetite, inducing weight loss, and treating obesity and obesity-related disorders.

DETAILED DESCRIPTION OF THE INVENTION

The invention relates to substituted 1,5,6,7-tetrahydropyrrolo-[3,2-c]pyridine (also called "pyrrolopiperidine") and substituted 1,5,6,7-tetrahydro-4H-pyrrolo[3,2-c]pyridin-4-one (also called "pyrrolopiperidinone") derivatives that have utility in the treatment of obesity. The present invention relates to the compound of Formula (I)

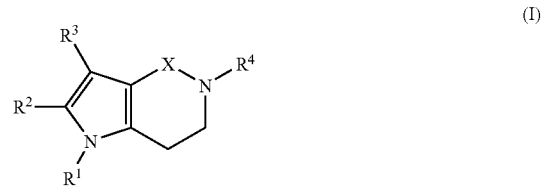

wherein
R$^1$ is phenyl optionally substituted with one or more halogen, (C$_1$–C$_6$)alkyl, (C$_1$–C$_6$)alkoxy, (C$_1$–C$_6$)alkylthio, trifluoromethyl, trifluoromethoxy, carboxyl, amino, cyano, nitro, (C$_1$–C$_6$)alkyl-carbonyl-amino, (C$_1$–C$_6$)alkyl-amino-carbonyl-amino, or phenyl optionally substituted with one or more halogen;
R$^2$ is a hydrogen,
halogen,
(C$_1$–C$_9$)alkyl optionally substituted with (C$_1$–C$_6$)alkoxy, trifluoromethyl, or with one or more fluorine,
phenyl optionally substituted with one or more halogen, (C$_1$–C$_6$)alkyl, (C$_2$–C$_8$)alkenyl, (C$_2$–C$_8$)alkynyl, (C$_1$–C$_6$)alkoxy, (C$_1$–C$_6$)alkyl-thio, trifluoromethyl, trifluoromethoxy, carboxyl, amino, cyano, nitro, $(C_1–C_6)$ alkyl-carbonyl-amino, $(C_1–C_6)$alkyl-amino-carbonyl-amino, or phenyl,
or
a 5- to 10-membered aromatic monocyclic or bicyclic heterocyclic radical optionally substituted with one or more halogen, $(C_1–C_6)$alkyl, $(C_1–C_6)$alkoxy, trifluoromethyl, trifluoromethoxy, cyano, or nitro;

$R^3$ is hydrogen, $(C_1–C_6)$alkyl, or benzyl;

X is —C(=O)— or $CH_2$;
provided that when X is —(C=O)—; $R^4$ is
hydrogen,
$(C_1–C_9)$alkyl optionally substituted with one or more hydroxy, benzyloxy, $(C_1–C_6)$alkoxy, trifluoromethyl, cyano, or fluorine,
benzyl or phenyl, optionally substituted on the phenyl ring with one or more $(C_1–C_6)$alkyl, hydroxy, $(C_1–C_6)$alkoxy, trifluoromethyl, cyano, nitro, or halogen,
piperidin-4-yl, piperidin-3-yl, or pyrrolidin-3-yl, each of which may be optionally substituted on the nitrogen atom of the piperidine or pyrrolidine ring with $(C_1–C_6)$alkyl, $(C_1–C_6)$hydroxyalkyl, benzyl, or phenyl, in which the benzyl or phenyl group may optionally be substituted on the phenyl ring with one or more halogen, $(C_1–C_6)$alkyl, $(C_1–C_6)$alkoxy, or trifluoromethyl,
—$NR^5R^6$ in which $R^5$ and $R^6$, taken together with the nitrogen atom to which they are attached, form a 5- to 10-membered saturated or unsaturated heterocyclic radical which is optionally substituted with one or more $(C_1–C_6)$alkyl, $(C_1–C_6)$alkoxy, hydroxy-substituted $(C_1–C_3)$alkyl, $(C_1–C_3)$alkoxy-substituted $(C_1–C_3)$alkyl, benzyl, phenyl, hydroxy, or fluorine,
or
a 5- to 10-membered aromatic monocyclic or bicyclic heterocyclic radical optionally substituted with one or more halogen, $(C_1–C_6)$alkyl, $(C_1–C_6)$alkoxy, trifluoromethyl, cyano, or nitro;

and when X=$CH_2$; $R^4$ is
$(C_2–C_6)$alkyl group,
cyclic $(C_3–C_7)$alkyl group which is optionally substituted with one or more $(C_1–C_6)$alkyl, hydroxy, $(C_1–C_6)$alkoxy, trifluoromethyl, cyano, or fluorine,
2-hydroxy-1-propyl group, substituted at the 3-position with a $(C_1–C_6)$alkoxy, benzyloxy, phenoxy, pyridinyloxy, or furylmethoxy group; in which the benzyloxy, phenoxy, pyridinyloxy, or furylmethoxy group is optionally substituted on the phenyl, pyridinyl, or furyl ring with one or more halogen, cyano, nitro, $(C_1–C_6)$alkyl, $(C_1–C_6)$alkoxy, or trifluoromethyl,
benzyl group which is substituted on the phenyl ring with one or more halogen, $(C_1–C_6)$alkyl, $(C_1–C_6)$ alkoxy, hydroxy, trifluoromethyl, cyano, nitro, $(C_1–C_6)$alkyl-carbonyl-amino, $(C_1–C_6)$alkyl-sulfonyl, $(C_1–C_6)$alkyl-amino, bis[$(C_1–C_6)$alkyl]-amino, or —$NR^5R^6$,
in which $R^5$ and $R^6$ of the —$NR^5R^6$ moiety, together with the nitrogen atom to which they are attached, form a 5- to 10-membered saturated or unsaturated heterocyclic radical optionally substituted with one or more $(C_1–C_6)$alkyl, $(C_1–C_6)$alkoxy, hydroxy, or fluorine,
phenyl substituted with one or more halogen, cyano, nitro, trifluoromethyl, $(C_1–C_6)$alkyl, $(C_1–C_6)$alkoxy, $(C_1–C_6)$alkyl-amino-carbonyl, $(C_1–C_6)$alkyl-amino sulfonyl, $(C_1–C_6)$alkyl-sulfonyl, or a phenyl group,
piperidin-4-yl, piperidin-3-yl, or pyrrolidin-3-yl, unsubstituted or substituted on the nitrogen atom of the piperidine or pyrrolidine ring with $(C_1–C_6)$alkyl, hydroxy-substituted $(C_1–C_6)$alkyl, $(C_1–C_3)$alkoxy-substituted $(C_1–C_3)$alkyl, benzyl, or a phenyl that is optionally substituted with one or more halogen, $(C_1–C_6)$alkyl, $(C_1–C_6)$alkoxy, trifluoromethyl, or cyano,
—(C=O)—$R^7$,
where $R^7$ is
$(C_1–C_9)$alkyl optionally substituted with one or more hydroxy, $(C_1–C_6)$alkoxy, trifluoromethyl, fluorine, benzyloxy, or phenoxy, in which the benzyloxy or phenoxy group may optionally be substituted on the phenyl ring with one or more halogen,
$(C_1–C_6)$alkoxy, benzyloxy, or phenoxy, each of which may optionally be substituted with one or more $(C_1–C_6)$alkyl, hydroxy, $(C_1–C_6)$alkoxy, trifluoromethyl, or fluorine,
phenyl, optionally substituted with one or more halogen, $(C_1–C_6)$alkyl, hydroxy-substituted $(C_1–C_6)$alkyl, $(C_1–C_6)$alkoxy, trifluoromethyl, trifluoromethoxy, hydroxy, cyano, nitro, bis[$(C_1–C_6)$alkyl]-amino, $(C_1–C_6)$alkyl-sulfonyl, $(C_1–C_6)$alkyl-sulfonyl-amino, $(C_1–C_6)$alkyl-carbonyl-amino, or $(C_1–C_6)$alkyl-amino-carbonyl-amino,
a 5- to 10-membered aromatic monocyclic or bicyclic heterocyclic radical, each of which may be optionally substituted with one or more halogen, $(C_1–C_6)$alkyl, $(C_1–C_6)$alkoxy, trifluoromethyl, cyano, or nitro,
—(C=O)$NR^8R^9$, where $R^8$ and $R^9$ are each independently
hydrogen,
$(C_1–C_9)$alkyl optionally substituted with one or more hydroxy, $(C_1–C_6)$alkoxy, benzyloxy, trifluoromethyl, cyano, or fluorine,
a 5- to 10-membered aromatic monocyclic or bicyclic heterocyclic radical optionally substituted with one or more halogen, $(C_1–C_6)$alkyl, $(C_1–C_6)$alkoxy, trifluoromethyl, cyano, or nitro,
phenyl optionally substituted with one or more halogen, $(C_1–C_6)$alkyl, $(C_1–C_6)$alkoxy, hydroxy, trifluoromethyl, trifluoromethoxy, cyano, or nitro, or
$R^8$ and $R^9$ may, together with the nitrogen atom to which they are attached, form a 5- to 10-membered saturated or unsaturated heterocyclic radical which is optionally substituted with one or more $(C_1–C_6)$alkyl, $(C_1–C_6)$alkoxy, hydroxy, hydroxy-substituted $(C_1–C_3)$alkyl, $(C_1–C_3)$ alkoxy-substituted $(C_1–C_3)$alkyl, benzyl, phenyl, or fluorine,
or
—$SO_2R^{10}$, where $R^{10}$ is
$(C_1–C_9)$alkyl optionally substituted with one or more hydroxy, $(C_1–C_6)$alkoxy, benzyloxy, trifluoromethyl, cyano, or fluorine,
benzyl in which the phenyl ring is optionally substituted with one or more $(C_1–C_6)$alkyl, $(C_1–C_6)$ alkoxy, trifluoromethyl, trifluoromethoxy, cyano, nitro, or halogen,
phenyl optionally substituted with one or more halogen, $(C_1–C_6)$alkyl, $(C_1–C_6)$alkoxy, hydroxy, trifluoromethyl, trifluoromethoxy, cyano, or nitro, 1- or 2-naphthyl optionally substituted with one or more halogen, $(C_1-C_6)$alkyl, $(C_1-C_6)$alkoxy, trifluoromethyl, cyano, bis[$(C_1-C_6)$alkyl]-amino, or $(C_1-C_6)$alkyl-amino, or a 5- to 10-membered aromatic monocyclic or bicyclic heterocyclic radical, optionally substituted with one or more halogen, $(C_1-C_6)$alkyl, $(C_1-C_6)$alkoxy, trifluoromethyl, cyano, or nitro;

and pharmaceutical salts and esters thereof.

The terms identified above have the following meaning throughout:

The term "halogen" means fluorine, chlorine, bromine, or iodine.

The terms "$(C_1-C_3)$alkyl," "$(C_1-C_6)$alkyl," "$(C_2-C_6)$alkyl, " and "$(C_1-C_9)$alkyl," mean $C_1-C_3$, $C_1-C_6$, $C_2-C_6$, and $C_1-C_9$ linear or branched alkyl groups, respectively, that may also includes a cyclic alkyl radical as part of the alkyl group. For example, this includes groups such as cyclopropyl, cyclohexyl, cyclopropyl-methyl, and cycloheptyl-methyl groups. The preferred alkyl groups are methyl, ethyl, propyl, and isopropyl groups.

The term "cyclic $(C_3-C_7)$alkyl" means a cyclic $C_3-C_7$ alkyl group, such as, for example, cyclopropyl, cyclopentyl, and cyclohexyl.

The term "$(C_2-C_8)$alkenyl" and "$(C_2-C_8)$alkynyl" mean $C_2-C_8$ linear or branched alkyl groups that contain a double or triple bond, respectively.

The term "$(C_1-C_3)$alkoxy" and "$(C_1-C_6)$alkoxy" mean a $(C_1-C_3)$alkyl-oxy and $(C_1-C_6)$alkyl-oxy group, respectively.

The phrase "5- to 10-membered saturated or unsaturated heterocyclic radical" means a fused or bridged, mono-, bi-, or tri-cyclic, non-aromatic heterocyclic radical which can contain one to three of the heteroatoms nitrogen, oxygen, or sulfur. These radicals include, for example, the following radicals: pyrrolidin-1-yl, piperidin-1-yl, piperazin-1-yl, hexahydroazepin-1-yl, azepan-1-yl, morpholin-4-yl, and thiomorpholin-4-yl.

The phrase "5- to 10-membered aromatic monocyclic or bicyclic heterocyclic radical" means a 5- or 6-membered aromatic heterocyclic radical or a fused bicyclic aromatic heterocyclic radical, which can contain one to three of the heteroatoms nitrogen, oxygen, or sulfur. These radicals include, for example, the following radicals: furyl, thienyl, isoxazolyl, pyridyl, pyrimidinyl, benzofuranyl, and benzothienyl.

When any moiety is described as being substituted, it can have one or more of the indicated substituents that can be located at any available position on the moiety. When there are two or more substituents on any moiety, each term shall be defined independently of any other in each occurrence.

Representative salts of the compounds of Formula I include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine salts and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

The esters in the present invention are non-toxic, pharmaceutically acceptable ester derivatives of the alcohols of Formula I. This includes ester derivatives prepared from acetic, benzoic, mandelic, stearic, lactic, salicylic, hydroxynaphthoic, glucoheptonic, and gluconic acid. The alcohol compounds of Formula I may be esterified by a variety of conventional procedures including reacting the appropriate anhydride, carboxylic acid, or acid chloride with the alcohol group of the Formula I compound. The appropriate anhydride is reacted with the alcohol in the presence of an acylation catalyst such as 1,8-bis[dimethylamino]naphthalene or DMAP (N,N-dimethylaminopyridine). An appropriate carboxylic acid may be reacted with the alcohol in the presence of a dehydrating agent such as dicyclohexylcarbodiimide, 1-[3-dimethylaminopropyl]-3-ethylcarbodiimide or other water soluble dehydrating agents which are used to drive the reaction by the removal of water, and optionally, an acylation catalyst. Esterification may also be reached using the appropriate carboxylic acid in the presence of trifluoroacetic anhydride and optionally, pyridine, or in the presence of N,N-carbonyldiimidazole with pyridine. Reaction of an acid chloride with the alcohol may be carried out with an acylation catalyst such as DMAP or pyridine. One skilled in the art would readily know how to successfully carry out these as well as other methods of esterification of alcohols. Sensitive or reactive groups on the compound of Formula I may need to be protected during any of the above methods for forming esters, and protecting groups may be added and removed by conventional methods well known in the art.

It will be appreciated that diastereomers and enantiomers of the exemplified structures will often be possible, and that pure isomers represent preferred embodiments. It is intended that pure stereoisomers, and mixtures thereof, are within the scope of the invention.

The compounds of this invention may, either by nature of asymmetric centers or by restricted rotation, be present in the form of isomers. Any isomer may be present in the (R)-, (S)-, or (R,S) configuration, preferably in the (R)- or (S)-configuration, whichever is most active.

All isomers, whether separated, pure, partially pure, or in racemic mixture, of the compounds of this invention are encompassed within the scope of this invention. The purification of said isomers and the separation of said isomeric mixtures may be accomplished by standard techniques known in the art.

Geometric isomers by nature of substituents about a double bond or a ring may be present in cis (=Z-) or trans (=E-) form, and both isomeric forms are encompassed within the scope of this invention.

The particular process to be utilized in the preparation of the compounds of this invention depends upon the specific compound desired. Such factors as the selection of the specific moieties and the specific substituents on the various moieties, all play a role in the path to be followed in the preparation of the specific compounds of this invention. These factors are readily recognized by one of ordinary skill in the art.

For synthesis of any particular compound, one skilled in the art will recognize that the use of protecting groups may be required for the synthesis of compounds containing certain substituents. A description of suitable protecting groups and appropriate methods of adding and removing such groups may be found in: Protective Groups in Organic Synthesis, Second Edition, T. W. Greene, John Wiley and Sons, New York, 1991.

In the Reaction Schemes below, one skilled in the art will recognize that reagents and solvents actually used may be selected from several reagents and solvents well known in the art to be effective equivalents. When specific reagents or solvents are shown in a Reaction Scheme, therefore, they are meant to be illustrative examples of conditions desirable for the execution of that particular Reaction Scheme. Abbreviations not identified in accompanying text are listed later in this disclosure under "Abbreviations and Acronyms."

Another object of this invention is to provide methods of making the compounds of the invention. The compounds may be prepared from readily available materials by the methods outlined in Reaction Schemes 1 and 2 below, and by obvious modifications thereto.

The present invention relates to the use of the compounds of this invention for the treatment of bulimia and obesity including associated dyslipidemia and other obesity- and overweight-related complications such as, for example, cholesterol gallstones, cancer (e.g., colon, rectum, prostate, breast, ovary, endometrium, cervix, gallbladder, and bile duct), menstrual abnormalities, infertility, polycystic ovaries, osteoarthritis, and sleep apnea, as well as for a number of other pharmaceutical uses associated therewith, such as the regulation of appetite and food intake, dyslipidemia, hypertriglyceridemia, Syndrome X, type II diabetes (non-insulin-dependent diabetes), atherosclerotic diseases such as heart failure, hyperlipidemia, hypercholesteremia, low HDL levels, hypertension, cardiovascular disease (including atherosclerosis, coronary heart disease, coronary artery disease, and hypertension), cerebrovascular disease and peripheral vessel disease. The compounds of this invention may also be useful for treating physiological disorders related to, for example, regulation of insulin sensitivity, inflammatory response, plasma triglycerides, HDL, LDL, and cholesterol levels and the like.

The compounds of Formula I of this invention are expected to be valuable as therapeutic agents. Accordingly, an embodiment of this invention includes a method of treating the various conditions identified above in a patient (including mammals) which comprises administering to said patient a composition containing an amount of the compound of Formula I that is effective in treating the target condition.

Compounds of Formula I may be administered alone or in combination with one or more additional therapeutic agents. Combination therapy includes administration of a single pharmaceutical dosage formulation which contains a compound of Formula I and one or more additional therapeutic agents, as well as administration of the compound of Formula I and each additional therapeutic agents in its own separate pharmaceutical dosage formulation. For example, a compound of Formula I and a therapeutic agent may be administered to the patient together in a single oral dosage composition such as a tablet or capsule, or each agent may be administered in separate oral dosage formulations.

Where separate dosage formulations are used, the compound of Formula I and one or more additional therapeutic agents may be administered at essentially the same time (e.g., concurrently) or at separately staggered times (e.g., sequentially).

For example, the compounds of Formula I may be used in combination with other therapies and drugs useful for the treatment of obesity, for example, in combination with $\beta_3$-adrenoreceptor agonists such as CL-316,243, or in combination with a drug compound that modulates digestion and/or metabolism such as drugs that modulate thermogenesis, lipolysis, gut motility, fat absorption, and satiety.

In addition, the compounds of Formula I may be administered in combination with one or more of the following hypoglycemic agents for the treatment of diabetes or diabetes-related disorders: insulin; biguanidines such as metformin or buformin; sulfonylureas such as acetohexamide, chloropropamide, tolazamide, tolbutamide, glyburide, glipizide, glyclazide; or any other insulin secretagogue such as, for example, repaglinide and nateglinide; or α-glycosidase inhibitors such as acarbose, voglibose, or miglitol. Also, the compounds of Formula I may be used in combination with HMG Co-A reductase inhibitors (statins), bile acid binding resin, or fibric acid derivatives to improve the lipid profile of subjects with dyslipidemia. Compounds of Formula I may also be used in combination with agents that regulate hypertension (e.g., inhibitors of angiotension converting enzyme (ACE), β-blockers, calcium channel blockers).

Furthermore, compounds of the present invention were determined, following oral dosing in rodents, to be present in significant concentrations in the brain. Therefore, the compounds of this invention may have utility for the treatment of any of various CNS (central nervous system) or psychological disorders, such as the treatment of substance or behavioral addiction, and the treatment of disorders associated with the use of psychotropic substances. Likewise, the compounds of this invention may have utility for the management and treatment of cognition and memory disorders.

The compounds of Formula I may also be utilized, in free base form or in compositions, as well as in research and diagnostics or as analytical reference standards, and the like, which are well known in the art. Therefore, the present invention includes compositions which are comprised of an inert carrier and an effective amount of a compound of Formula I, or a salt, or ester thereof. An inert carrier is any material which does not interact with the compound to be carried and which lends support, means of conveyance, bulk, traceable material, and the like to the compound to be carried. An effective amount of the compound is that amount which produces a result or exerts an influence on the particular procedure being performed.

It is anticipated that prodrug forms of the compounds of this invention will prove useful in certain circumstances, and such compounds are also intended to fall within the scope of the invention. Prodrug forms may have advantages over the parent compounds exemplified herein, in that they are better absorbed, better distributed, more readily penetrate the central nervous system, are more slowly metabolized or cleared. Prodrug forms may also have formulation advantages in terms of crystallinity or water solubility. For example, compounds of the invention having one or more hydroxyl groups may be converted to esters or carbonates bearing one or more carboxyl, hydroxyl, or amino groups, which are hydrolyzed at physiological pH values or are cleaved by endogenous esterases or lipases in vivo. See, for example, U.S. Pat. Nos. 4,942,184; 4,960,790; 5,817,840; and 5,824, 701 (all of which are incorporated herein by reference in their entirety), and references therein.

An object of this invention is to provide a method of inducing weight loss in an individual by administration of a compound of the invention. The method of the invention comprises administering to an individual a therapeutically effective amount of at least one compound of the invention, or a prodrug thereof, which is sufficient to induce weight loss. The invention further comprises a method of preventdropyrrolopyridine compound of Formula (V). Removal of the protecting group gives the compound of Formula (VI). Incorporation of the $R^4$ group onto (VII) (for example, by N-alkylation or N-acylation under basic conditions) gives the Formula (Ia) compound.

Alternatively, the pyrrolopiperidinone compound of Formula (VI) may be reduced with reagents such as borane-THF complex to provide (Ia). Formula (VI) compounds are prepared as described in detail in Reaction Scheme 2, below.

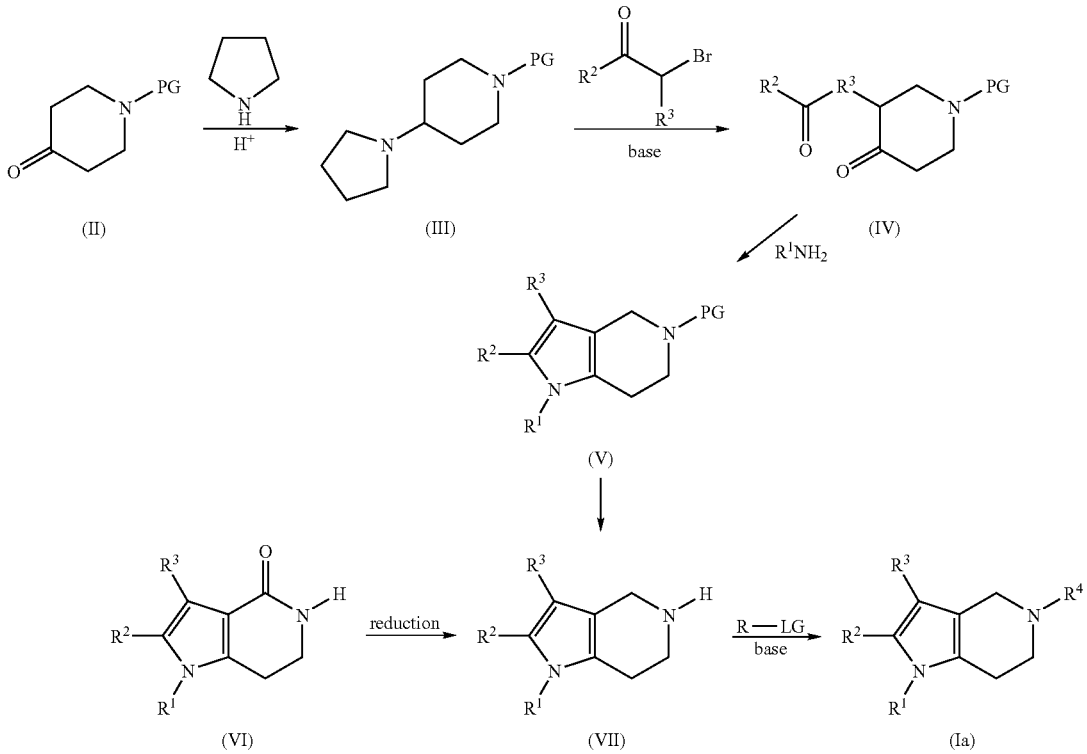

Reaction Scheme 1

PG = protecting group, e.g. benzyl, benzyloxycarbonyl, etc.
LG = leaving roup, e.g., halo, TsO, or MsO, etc.

ing weight gain in an individual by administering an amount of at least one compound of the invention, or a prodrug thereof, which is sufficient to prevent weight gain.

Another object of this invention is to provide methods of making the compounds of the invention. The compounds may be prepared from readily available materials by the methods outlined below, and by obvious modifications thereto.

General Preparation of Compounds of Formula I

Preparation of compounds of Formula Ia may be accomplished as shown in Reaction Scheme 1, starting from readily available 4-piperidinones, N-protected with a group such a benzyloxycarbonyl, or the like. Using a method related to that described in (a) Borne, et al., J. Med. Chem. 27:1274, 1984; (b) Archibald, U.S. Pat. No. 3,992,544; (c) Nagai et al., Chem. Pharm. Bull. 25:1911–1922, 1977; and (d) Nagarajan, et al., Ind. J. Chem. 24B:98–111, 1985; the piperidinone (II) is converted to an enamine (III), which is then allowed to react with a 2-bromoketone under basic conditions to give a 1,4-diketone of Formula (IV). Reaction of (IV) with an amine of Formula $R^1NH_2$, in a solvent such as acetic acid with heating at reflux, provides the tetrahy- Compounds of the invention of Formula (Ib) are prepared as described in Reaction Scheme 2. Michael addition of an amine of Formula $R^4NH_2$ to an acrylic ester (VIII) gives the 3-amino ester of Formula IX; N-acylation of (IX) with a malonyl chloride in the presence of base gives the diester amide of Formula (X). The compound of Formula (X) cyclizes in base to give a compound of Formula (XI), which may be hydrolyzed and decarboxylated under acidic conditions to give a ketopiperidinone of Formula (XII). The reaction of the Formula (XII) compound with an amino ketone of Formula $R^1NHCH_2COR^1$ provides a cyclized compound of Formula (XIII) [i.e., Formula (Ib) where $R^2$=H]. The introduction of an $R^2$ group may be accomplished by bromination of (XI) followed by a coupling reaction with an organoborane, in the presence of a palladium catalyst (e.g, $Pd(PPh_3)_4$) and a base such as, for example, sodium carbonate. Removal of the $R^4$ group in Formula (XIII) can be achieved in some cases, depending on the structure of $R^4$ and the reaction conditions required for cleaving the nitrogen—$R^4$ bond, by methods known in the art. For example, $R^4$ groups which are acid labile, such as, for example, $R^4$=2,4-dimethoxy-benzyl, under acidic conditions (e.g., TFA) provides a compound of Formula (VI) [i.e., Formula (Ib) where $R^4$=H]. The compound of Formula (VI) may be used to prepare a variety of Formula Ia compounds as described in Reaction Scheme 1. In addition, (VI) may be used to prepare additional Formula Ib compounds, such as by reaction with a compound of Formula $R^4$-LG, where LG is a leaving group such as halogen, usually under basic reaction conditions.

It will be recognized by those skilled in the art that substituents (e.g., $R^4$) present on compounds of Formula (Ia) and (Ib) may be further elaborated by straightforward means to create additional examples of compounds of the invention. For example, a compound of Formula (Ib) where $R^4$ is a 2-benzyloxy-cyclohexyl may be converted to the compound where $R^4$ is a 2-hydroxy-cyclohexyl substituent by reaction with TMSI. Similarly, other substituents at other positions may be inter-converted by hydrolysis, oxidation, or reduction, employing the use of protecting groups as appropriate, as is well known in the art.

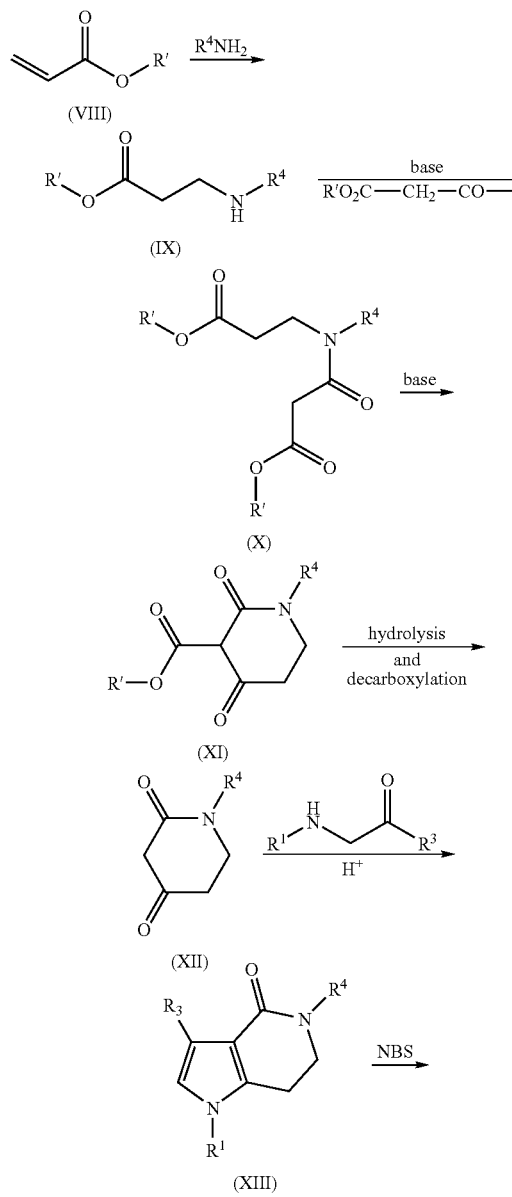

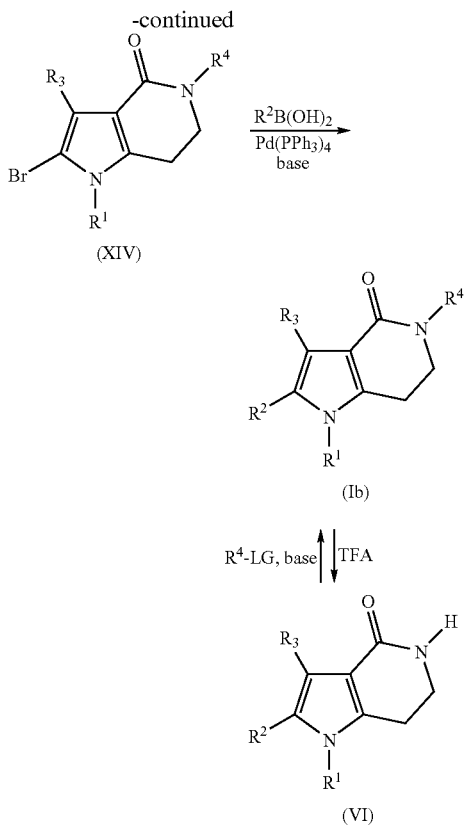

R' = lower alkyl
LG = halo, TsO, etc.

EXPERIMENTAL EXAMPLES

The following specific preparative examples are included as illustrations of preparation of specific compounds of the invention, and are not to be construed as limiting the scope of the invention in any way.

NMR Methods:

Proton ($^1$H) nuclear magnetic resonance (NMR) spectra were measured with a General Electric GN-Omega 300 (300 MHz) spectrometer with either Me$_4$Si ($\delta$ 0.00) or residual protonated solvent (CHCl$_3$ $\delta$ 7.26; MeOH $\delta$ 3.30; DMSO $\delta$ 2.49) as reference standard. Carbon ($^{13}$C) NMR spectra were measured with a General Electric GN-Omega 300 (75 MHz) spectrometer with solvent (CDCl$_3$ $\delta$ 77.0; d$_3$-MeOD; $\delta$ 49.0; d$_6$-DMSO $\delta$ 39.5) as reference standard.

LC-MS Instrumentation:

(a) Gilson HPLC system equipped with two Gilson 306 pumps, a Gilson 215 Autosampler, a Gilson diode array detector, a YMC Pro C-18 column (2×23 mm, 120 A), and a Micromass LCZ single quadrupole mass spectrometer with z-spray electrospray ionization. Spectra were scanned from 120–800 amu over 1.5 seconds. ELSD (Evaporative Light Scattering Detector) data was also acquired as an analog channel.

(b) Hewlett-Packard 1100 HPLC equipped with a quaternary pump, a variable wavelength detector set at 254 nm, a YMC pro C-18 column (2×23 mm, 120 A), and a Finnigan LCQ ion trap mass spectrometer with electrospray ionization. Spectra were scanned from 120–1200 amu using a variable ion time according to the number of ions in the source.

HPLC Conditions:

In the Examples and Tables provided below, LC-MS data are given with retention times (RT) determined by using one of the following methods.

Method 1. Eluants were A: 2% acetonitrile in water with 0.02% TFA, and B: 2% water in acetonitrile with 0.02% TFA. Elution conditions consisted of a flow rate of 1.0 mL/min with an initial hold at 10% B for 0.5 minutes, followed by gradient elution from 10% B to 95% B over 3.5 minutes, followed by a final hold at 95% B for 0.5 minutes. Total run time was 6.5 minutes.

Method 2. Eluants as above; elution at a flow rate of 1.5 mL/min with an initial hold at 10% B for 0.5 minutes, followed by gradient elution from 10% B to 90% B over 3.5 minutes, followed by a final hold at 90% B for 0.5 minutes. Total run time was 4.8 minutes.

Abbreviations and Acronyms

When the following abbreviations are used herein, they have the following meaning:

| | |
|---|---|
| Celite ® | diatomaceous earth filter agent, ® Celite Corp. |
| DMAP | 4-(N,N-dimethylamino)pyidine |
| DME | dimethoxyethane |
| DMF | N,N-dimethylformamide |
| DMSO | dimethylsulfoxide |
| ELSD | evaporative light scattering detector |
| EtOAc | ethyl acetate |
| $Et_2O$ | diethyl ether |
| $Et_3N$ | triethylamine |
| h | hour(s) |
| HPLC | high performance liquid chromatography |
| LC-MS | liquid chromatography-mass spectroscopy |
| min | minute(s) |
| m/z | mass-to-charge ratio |
| MeCN | acetonitrile |
| Ms | methanesulfonyl |
| NBS | N-bromosuccinimide |
| OMs | methanesulfonyl-oxy |
| OTs | 4-toluenesulfonyl-oxy |
| Rf | retention factor (TLC) |
| RT | retention time (HPLC) |
| rt | room temperature |
| THF | tetrahydrofuran |
| TFA | trifluoroacetic acid |
| TLC | thin layer chromatography |
| Ts | 4-toluenesulfonyl |

Example 1

Preparation of 5-benzyl-2-(4-chlorophenyl)-3-methyl-1-(2-methylphenyl)-4,5,6,7-tetrahydro-1H-pyrrolo-[3,2-c]pyridine

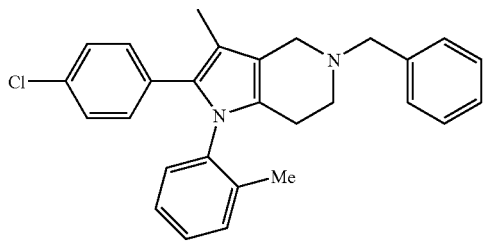

The preparation of this and other pyrrolopyridines was carried out in three steps using the methods described by (a) Borne, et al., J. Med. Chem. 27:1274, 1984; (b) Archibald, U.S. Pat. No. 3,992,544; (c) Nagai, et al., Chem. Pharm. Bull. 25:1911–1922, 1977; (d) Nagarajan, et al., Ind. J. Chem. 24B:98–111, 1985. The following example is illustrative of the third, or ring-forming step.

To a solution of 4-anilino-2-[2-(4-chlorophenyl)-1-methyl-2-oxoethyl]-cyclohexanone (1.58 g, 4.46 mmol) in AcOH (15 mL) at rt was added o-toluidine (478 mg, 4.46 mmol). The resulting solution was heated at reflux for 2 h. The cooled solution was treated with 1N NaOH and NaOH pellets until a pH of 10 was achieved. EtOAc was added and the phases were separated. The combined organic extracts were dried over $MgSO_4$, and evaporated. The residue was purified by flash chromatography using 10% to 50% AcOEt/hexane as eluant to give the title material (1.66 g, 88% yield). LC-MS m/z (MH$^+$) 427, retention time 2.70 min (method 2).

Example 2

Preparation of 1-(2-chlorophenyl)-2-(4-methoxyphenyl)-4,5,6,7-tetrahydro-1H-pyrrolo [3.2-c]pyridine

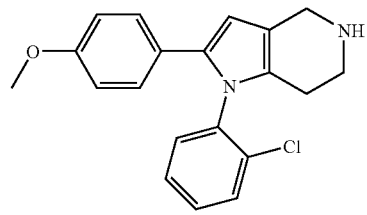

A solution of N-carbobenzyloxy (CBZ) protected amine (5.4 g, 11.4 mmol; prepared by methods as described in Example 1) in THF (25 mL) was added to Pd/C catalyst (1.08 g, Degussa type) in 10 mL THF. The mixture was stirred under a hydrogen atmosphere for 2 h. The mixture was filtered and the filtrate was evaporated. The residue was purified by silica gel column, eluting with ethyl acetate, followed by 20% methanol in ethyl acetate. The product was obtained as a pale yellow solid (3.06 g, 79%). LC-MS m/z (MH$^+$) 339.2, retention time 1.85 min (method 1). An alternative procedure, using potassium tert-butoxide to remove the CBZ group, was carried out according to the method described in J. Amer. Chem. Soc., 109:1587, 1987.

In a similar manner, 1-(2-chlorophenyl)-2-(4-chlorophenyl)-4,5,6,7-tetrahydro-1H-pyrrolo[3,2-c]pyridine was prepared; LC-MS m/z (MH$^+$) 343, retention time 2.48 min (method 1).

Example 3

Preparation of 2-(4-methoxyphenyl)-1-(2-methylphenyl)-4,5,6,7-tetrahydro-1H-pyrrolo [3,2-c]pyridine

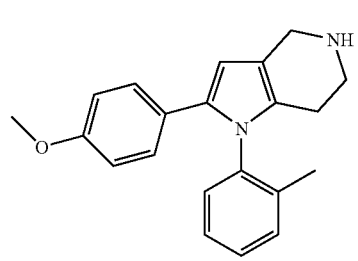

5-Benzyl-2-(4-methoxyphenyl)-1-(2-methylphenyl)4,5,6,7-tetrahydro-1H-pyrrolo[3,2-c]pyridine (5.6 g, 14 mmol;

prepared by methods as described in Example 1) was added to a suspension of palladium hydroxide on carbon (20%, 1.52 g, 2 mmol) in dry methanol (130 mL) and tetrahydrofuran (100 mL) under argon. The mixture was degassed by vacuum, and purged by argon several times. Then, the flask was fitted with a balloon containing hydrogen gas, and the mixture was stirred under $H_2$ at rt overnight. The reaction mixture was filtered through Celite, and the filtrate evaporated to provide the product (4.3 g, 98%). LC-MS m/z ($MH^+$) 409.2, retention time 2.30 min (method 2).

In a similar manner, 2–4-chlorophenyl)-3-methyl-1-(2-methylphenyl)4,5,6,7-tetrahydro-1H-pyrrolo[3,2-c]pyridine was prepared; LC-MS m/z ($MH^+$) 336, retention time 2.46 min (method 2).

Example 4

Preparations of 1-(2-chlorophenyl)-2-(4-chlorophenyl)-3-methyl-4,5,6,7-tetrahydro-1H-pyrrolo[3,2-c]pyridine

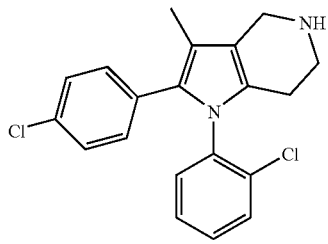

To a solution of 1-(2-chlorophenyl)-2-(4-chlorophenyl)-3-methyl-1,5,6,7-tetrahydro-4H-pyrrolo[3,2-c]pyridin-4-one (2.84 g, 7.64 mmol, prepared as in Scheme 2 and in a similar manner to Example 22) in tetrahydrofuran (38 mL) was added borane-tetrahydrofuran complex (1 M, 76 mL) at 0° C. over 20 minutes. The mixture was heated at reflux for 3 h. The mixture was cooled to rt, methanol was added, and then the solvent was evaporated off. The residue was purified by silica gel chromatography. Elution first with ethyl acetate, followed by 10% methanol in methylene chloride, gave a colorless gum (950 mg, 34.8%). LC-MS m/z ($MH^+$) 357.1, retention time 2.78 min (method 2).

Example 5

Preparation of 1-(2-chlorophenyl)-2-(4-methoxyphenyl)-5-(methylsulfonyl)-4,5,6,7-tetrahydro-1H-pyrrolo-[3,2-c]pyridine

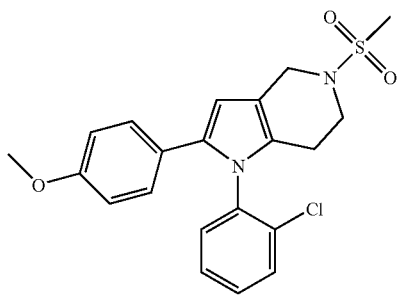

To an 8-mL vial charged with piperidinomethyl polystyrene (3.57 mmol/g, 99.2 mg, 0.354 mmol) and a solution of 1-(2-chlorophenyl)-2-(4-methoxyphenyl)-4,5,6,7-tetrahydro-1H-pyrrolo[3,2-c]pyridine (Example 2), 40.0 mg, 0.118 mmol) in 4 mL dichloromethane was added methanesulfonyl chloride (18.2 μL, 0.236 mmol). The reaction mixture was mixed by orbital shaking for 4 h. The solid was removed by filtration. The filtrate was evaporated, and the residue was purified by preparative reversed-phase HPLC to give a solid (19.8 mg, 40%): $R_f$=0.20 (1:2 EtOAc/hexanes).

Example 6

Preparation of 5-(3-chlorobenzoyl)-1-(2-chlorophenyl)-2-(4-methoxyphenyl)4,5,6,7-tetrahydro-1H-pyrrolo[3,2-c]pyridine

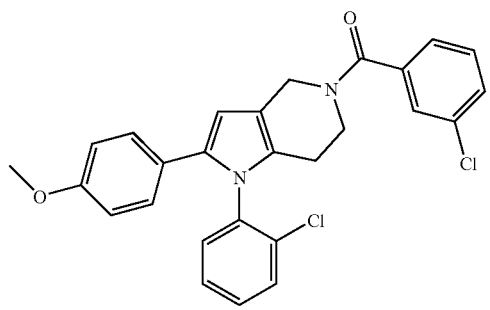

To an 8-mL vial charged with piperidinomethyl polystyrene (3.57 mmol/g, 198.4 mg, 0.708 mmol) and a solution of 1-(2-chlorophenyl)-2-(4-methoxyphenyl)-4,5,6,7-tetrahydro-1H-pyrrolo[3,2-c]pyridine (Example 2, 80.0 mg, 0.236 mmol) in 3 mL dichloromethane was added 3-chlorobenzoyl chloride (62.0 mg, 0.0.54 mmol). The reaction mixture was mixed by orbital shaking for 3 h. The solid was removed by filtration. The filtrate was evaporated, and the residue was purified on silica gel eluting with 1:5 EtOAc/hexanes to give a solid (83.2 mg, 74%): $R_f$=0.19 (1:2 EtOAc/hexanes).

Example 7

Preparation of 4-[1-(2-chlorophenyl)-2-(4-methoxyphenyl)-1,4,6,7-tetrahydro-5H-pyrrolo[3,2-c]pyridin-5-yl]benzonitrile

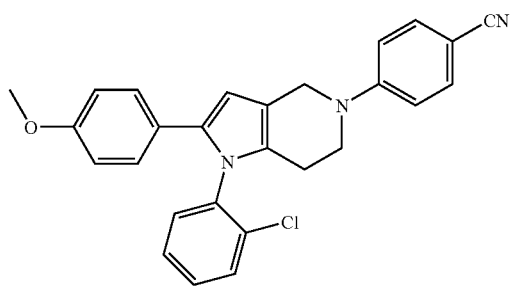

To a suspension of 1-(2-chlorophenyl)-2-(4-methoxyphenyl)-4,5,6,7-tetrahydro-1H-pyrrolo[3,2-c]pyridine (Example 2, 80.0 mg, 0.236 mmol) and $K_2CO_3$ (97.9 mg, 0.708 mmol) in 2 mL DMF was added 4-fluorobenzonitrile (86.0 mg, 0.472 mmol) under argon. The mixture was heated at 130° C. with stirring for 48 h. The mixture was cooled to rt, water was added, and the mixture was extracted with ethyl acetate. The organic layer was dried over Na₂SO₄ and evaporated under reduced pressure. The crude product was purified on silica gel eluting with 1:3 EtOAc/hexanes to give a solid (44.7 mg, 43%): R_f=0.32 (1:2 EtOAc/hexanes).

Example 8

Preparation of 1-(2-chlorophenyl)-2-(4-chlorophenyl)-3-methyl)-1,4,6,7-tetrahydro-5H-pyrrolo[3,2-c]pyridine-5-carboxamide

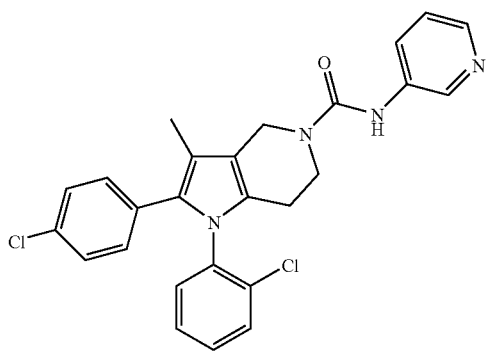

A solution of 2-(4-chlorophenyl)-3-methyl-1-(2-chlorophenyl)-4,5,6,7-tetrahydro-1H-pyrrolo[3,2-c]pyridine (Example 4, 30 mg, 0.084 mmol), 3-isocyanatopyridine (10.5 mg, 0.0874 mmol), 4-dimethylaminopyridine (5 mg, 0.04 mmol), and triethylamine (12 μL, 0.084 mmol) in methylene chloride (5 mL) was stirred at rt overnight. The solvent was evaporated, and the residue was purified by HPLC. The urea product 1-(2-chlorophenyl)-2-(4-chlorophenyl)-3-methyl-N-(3-pyridinyl)-1,4,6,7-tetrahydro-5H-pyrrolo[3,2-c]pyridine-5-carboxamide (1.4 mg, 3.5%) was obtained as a TFA salt. LC-MS m/z (MH⁺) 477.1, retention time 2.41 min (method 2).

Example 9

Preparation of 1-(2-chlorophenyl)-5-(4-fluorobenzyl)-2-(4-methoxyphenyl)-4,5,6,7-tetrahydro-1H-pyrrolo-[3,2-c]pyridine

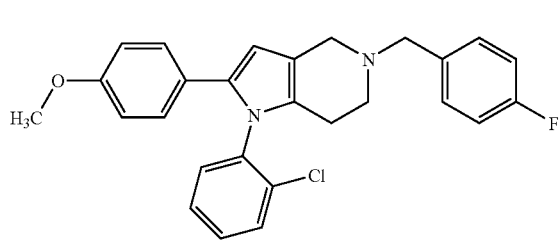

A solution of 1-(2-chlorophenyl)-2-(4-methoxyphenyl)-4,5,6,7-tetrahydro-1H-pyrrolo[3,2-c]pyridine (Example 2, 677.7 mg, 0.50 mmol), 4-fluorobenzaldehyde (0.13 mL, 0.60 mmol), acetic acid (0.03 mL, 0.60 mmol), and NaBH(OAc)₃ (148.4 mg, 0.70 mmol) in methylene chloride (15 mL) was stirred at rt for 24 h. Sodium hydroxide (1N) was added, and the solution was extracted with diethyl ether (3×30 mL). The combined ether layers were dried (sodium sulfate), filtered, and evaporated. The residue was purified by silica gel column, eluting with 3:1 hexanes:ethyl acetate. The product was isolated as a white solid (218.1 mg, 97%). LC-MS m/z (MH⁺) 447, retention time 2.65 min (method 1).

Example 10

Preparation of trans-2-[1-(2-chlorophenyl)-2(-4-methoxyphenyl)-1,4,6,7-tetrahydro-5H-pyrrolo[3,2-c]pyridin-5-yl]cyclohexanol

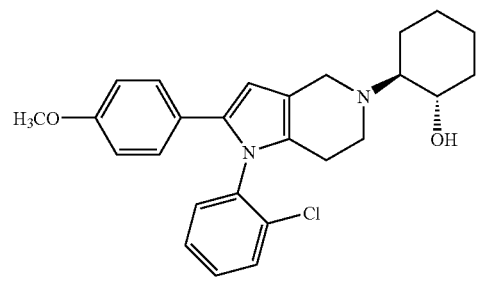

A solution of 1-(2-chlorophenyl)-2-(4-methoxyphenyl)-4,5,6,7-tetrahydro-1H-pyrrolo[3,2-c]pyridine (Example 2, 500 mg, 1.33 mmol), cyclohexene oxide (1.34 mL, 13.3 mmol), and triethylamine (0.55 mL, 3.99 mmol) in ethanol (14 mL) was heated at reflux for 20 h. The solution was cooled to rt, and evaporated. The residue was purified by silica gel column, eluting with 3:1 to 2:1 hexanes:ethyl acetate. The product, racemic trans-2-[1-(2-chlorophenyl)-2-(4-methoxyphenyl)-1,4,6,7-tetrahydro-5H-pyrrolo[3,2-c]pyridin-5-yl]cyclohexanol, was isolated as a pale yellow solid (398 mg, 63%). LC-MS m/z (MH⁺) 437.1, retention time 2.45 min (method 1).

Example 11

Preparation of 1-[1-(2-chlorophenyl)-2-(4-methoxyphenyl)-1,4,6,7-tetrahydro-5H-pyrrolo[3,2 -c]pyridin-5-yl]-3-{[3-(trifluoromethyl)-2-pyridinyl]oxy}-2-propanol

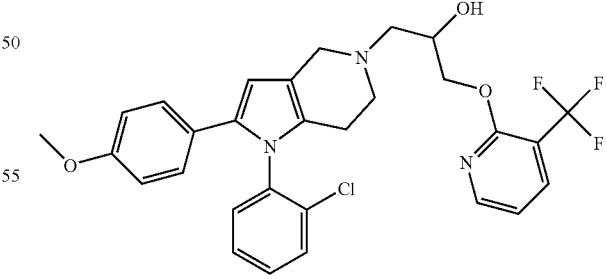

In a 8-mL screw-cap vial, 1-(2-chlorophenyl)-2-4-methoxyphenyl)-4,5,6,7-tetrahydro-1H-pyrrolo[3,2-c]pyridine (Example 2, 33.8 mg, 0.1 mmol), 2-(oxiran-2-ylmethoxy)-3-(trifluoromethyl)pyridine (21.9 mg, 0.1 mmol), and 1 mL 9:1 dioxane/H₂O were added. The reaction mixture was mixed by orbital shaking at 80° C. for 2 days. The mixture was cooled to rt, and the solvent was evaporated. The residue was dissolved in 2 mL MeOH and purified by preparative reversed-phase HPLC. The collected HPLC fraction was evaporated, treated with 10 mL saturated $Na_2CO_3$ solution, and then extracted with 20 mL dichloromethane. A solution of 2M HCl in diethyl ether (5 mL) was added to the organic layer, and the solvents were evaporated to give the product HCl salt as a brown solid (28 mg, 44.4%). 1H NMR (400 MHz, $CD_3COCD_3$) δ 7.71 (m, 2H), 7.45 (m, 1H), 7.40–7.10 (m, 3 H), 6.90 (d, 2 H), 6.63 (d, 2 H), 6.23 (m, 1H), 6.05 (s, 1H), 4.50 (m, 2H), 4.30 (m, 3H), 3.9 (m, 1H), 3.65 (s, 3H), 3.55 (m, 1H), 3.35 (m, 1H), 3.15 (m, 1H), 2.61 (s, 2H); LC-MS m/z 558 (MH+), retention time 2.41 min (method 2).

Using appropriate starting materials and the experimental procedures described above for Examples 1–11, compounds appearing in Table 1 were prepared. LC-MS characterization of compounds, was carried out by using the instrumentation and methods set forth above.

TABLE 1

| Entry No. | R¹ | R² | R³ | R⁴ | IUPAC Name | MS m/z (MH+) | TLC Rf (solvent) | HPLC RT (min) | HPLC Method | Synthesis Method of Ex. No. |
|---|---|---|---|---|---|---|---|---|---|---|
| 1 | 2-Cl—Ph | 4-Cl—Ph | H | benzyloxy-carbonyl | benzyl 1-(2-chlorophenyl)-2-(4-chlorophenyl)-1,4,6,7-tetrahydro-5H-pyrrolo[3,2-c]pyridine-5-carboxylate | 477 | 0.58 (2:1 Hexane/EtOAc) | 4.16 | 1 | 1 |
| 2 | 2-Cl—Ph | 4-MeO—Ph | H | cyclohexyl | 1-(2-chlorophenyl)-5-cyclohexyl-2-(4-methoxyphenyl)-4,5,6,7-tetrahydro-1H pyrrolo[3,2-c]pyridine hydrochloride | 421 | | 2.63 | 1 | 5,6,7,8,9,10,11 |
| 3 | 2-Cl—Ph | 4-MeO—Ph | H | trans-2-hydroxy-cyclohexyl | trans-2-[1-(2-chlorophenyl)-2-(4-methoxyphenyl)-1,4,6,7-tetrahydro-5H-pyrrolo[3,2-c]pyridin-5-yl]cyclohexanol hydrochloride | 437 | | 2.45 | 1 | 5,6,7,8,9,10,11 |
| 4 | 2-Cl—Ph | 4-Cl—Ph | H | benzyl | 5-benzyl-1-(2-chlorophenyl)-2-(4-chlorophenyl)-4,5,6,7-tetrahydro-1H-pyrrolo[3,2-c]pyridine hydrochloride | 433 | 0.39 (1:2 EtOAc/Hexane) | 2.71 | 1 | 5,6,7,8,9,10,11 |
| 5 | 2-Cl—Ph | 4-MeO—Ph | H | 4-fluorobenzyl | 1-(2-chlorophenyl)-5-(4-fluorobenzyl)-2-(4-methoxyphenyl)-4,5,6,7-tetrahydro-1H-pyrrolo[3,2-c]pyridine hydrochloride | 447 | | 2.65 | 1 | 5,6,7,8,9,10,11 |
| 6 | 2-Cl—Ph | 4-Cl—Ph | H | benzyl | 5-benzyl-1-(2-chlorophenyl)-2-(4-chlorophenyl)-4,5,6,7-tetrahydro-1H-pyrrolo[3,2-c]pyridine hydrochloride | 433 | | 2.83 | 1 | 5,6,7,8,9,10,11 |
| 7 | 2-Cl—Ph | 4-Cl—Ph | H | H | 1-(2-chlorophenyl)-2-(4-chlorophenyl)-4,5,6,7-tetrahydro-1H-pyrrolo[3,2-c]pyridine hydrochloride | 343 | 0.08 (1:9 MeOH/EtOAc) | 2.48 | 1 | 2,3 |
| 8 | 2-Cl—Ph | 4-MeO—Ph | H | benzyloxy-carbonyl | benzyl-(2-chlorophenyl)-2-(4-methoxyphenyl)-1,4,6,7-tetrahydro-5H-pyrrolo[3,2-c]pyridine-5-carboxylate | 473 | 0.55 (2:1 Hexane/EtOAc) | 3.95 | 1 | 1 |
| 9 | 2-Cl—Ph | 4-MeO—Ph | H | H | 1-(2-chlorophenyl)-2-(4-methoxyphenyl)-4,5,6,7-tetrahydro-1H-pyrrolo[3,2-c]pyridine | 339 | 0.05 (2:1 Hexane/EtOAc) | 1.85 | 1 | 2,3 |
| 10 | 2-Cl—Ph | 4-MeO—Ph | H | acetyl | 5-acetyl-1-(2-chlorophenyl)-2-(4-methoxyphenyl)-4,5,6,7-tetrahydro-1H-pyrrolo[3,2-c]pyridine | 382 | 0.05 (1:2 EtOAc/Hexane) | 3.02 | 1 | 5,6,7,8,9,10,11 |
| 11 | 2-Cl—Ph | 4-MeO—Ph | H | 2,2-dimethyl-propanoyl | 1-(2-chlorophenyl)-5-(2,2-dimethylpropanoyl)-2-(4-methoxyphenyl)-4,5,6,7-tetrahydro-1H-pyrrolo[3,2-c]pyridine | 424 | 0.27 (1:2 EtOAc/Hexane) | 3.60 | 1 | 1 |
| 12 | 2-Cl—Ph | 4-MeO—Ph | H | cyclohexyl-carbonyl | 1-(2-chlorophenyl)-5-(cyclohexylcarbonyl)-2-(4-methoxyphenyl)-4,5,6,7-tetrahydro-1H-pyrrolo[3,2-c]pyridine | 450 | 0.22 (1:2 EtOAc/Hexane) | 3.74 | 1 | 5,6,7,8,9,10,11 |
| 13 | 2-Cl—Ph | 4-MeO—Ph | H | 1-pyrrolidinyl-carbonyl | 1-(2-chlorophenyl)-2-(4-methoxyphenyl)-5-(1-pyrrolidinylcarbonyl)-4,5,6,7-tetrahydro-1H-pyrrolo[3,2-c]pyridine | 437 | 0.06 (1:2 EtOAc/Hexane) | 3.38 | 1 | 5,6,7,8,9,10,11 |
| 14 | 2-Cl—Ph | 4-MeO—Ph | H | 4-fluoro-benzoyl | 1-(2-chlorophenyl)-5-(4-fluorobenzoyl)-2-(4-methoxyphenyl)-4,5,6,7-tetrahydro-1H pyrrolo[3,2-c]pyridine | 462 | 0.15 (1:2 EtOAc/Hexane) | 3.63 | 1 | 5,6,7,8,9,10,11 |
| 15 | 2-Cl—Ph | 4-MeO—Ph | H | 2-trifluoro-methyl-benzoyl | 1-(2-chlorophenyl)-2-(4-methoxyphenyl)-5-[2-(trifluoromethyl)benzoyl]-4,5,6,7-tetrahydro-1H-pyrrolo[3,2-c]pyridine | 512 | 0.19 (1:2 EtOAc/Hexane) | 3.68 | 1 | 5,6,7,8,9,10,11 |
| 16 | 2-Cl—Ph | 4-MeO—Ph | H | 3-trifluoro-methyl-benzoyl | 1-(2-chlorophenyl)-2-(4-methoxyphenyl)-5-[3-(trifluoromethyl)benzoyl]-4,5,6,7-tetrahydro-1H-pyrrolo[3,2-c]pyridine | 512 | 0.22 (1:2 EtOAc/Hexane) | 3.78 | 1 | 5,6,7,8,9,10,11 |

TABLE 1-continued

| Entry No. | R¹ | R² | R³ | R⁴ | IUPAC Name | MS m/z (MH+) | TLC Rf (solvent) | HPLC RT (min) | HPLC Method | Synthesis Method of Ex. No. |
|---|---|---|---|---|---|---|---|---|---|---|
| 17 | 2-Cl—Ph | 4-MeO—Ph | H | 4-trifluoromethyl-benzoyl | 1-(2-chlorophenyl)-2-(4-methoxyphenyl)-5-[4-(trifluoromethyl)benzoyl]-4,5,6,7-tetrahydro-1H-pyrrolo[3,2-c]pyridine | 512 | 0.24 (1:2 EtOAc/Hexane) | 3.80 | 1 | 5,6,7,8,9 10,11 |
| 18 | 2-Cl—Ph | 4-Cl—Ph | H | trans-2-hydroxy-cyclohexyl | trans-2-[1-(2-chlorophenyl)-2-(4-chlorophenyl)-1,4,6,7-tetrahydro-5H-pyrrolo[3,2-c]pyridin-5-yl]cyclohexanol hydrochloride | 441 | | 2.68 | 1 | 5,6,7,8,9 10,11 |
| 19 | 2-Cl—Ph | 4-MeO—Ph | H | cyclopentyl | 1-(2-chlorophenyl)-5-cyclopentyl-2-(4-methoxyphenyl)-4,5,6,7-tetrahydro-1H-pyrrolo[3,2-c]pyridine hydrochloride | 407 | | 2.54 | 1 | 5,6,7,8,9, 10,11 |
| 20 | 2-Cl—Ph | 4-MeO—Ph | H | 4-dimethylamino-benzyl | 4-{[1-(2-chlorophenyl)-2-(4-methoxyphenyl)-1,4,6,7-tetrahydro-5H-pyrrolo[3,2-c]pyridin-5-yl]methyl56 -N,N-dimethylaniline dihydrochloride | 472 | | 2.65 | 1 | 5,6,7,8,9 10,11 |
| 21 | 2-Cl—Ph | 4-MeO—Ph | H | benzyloxy-carbonyl | benzyl 4-[1-(2-chlorophenyl)-2-(4-methoxyphenyl)-1,4,6,7-tetrahydro-5H-pyrrolo[3,2-c]pyridin-5-yl]-1-piperidinecarboxylate hydrochloride | 556 | | 2.79 | 1 | 5,6,7,8,9 10,11 |
| 22 | 2-Cl—Ph | 4-MeO—Ph | H | methyl-sulfonyl | 1-(2-chlorophenyl)-2-(4-methoxyphenyl)-5-(methylsulfonyl)-4,5,6,7-tetrahydro-1H-pyrrolo[3,2-c]pyridine | 417 | 0.20 (1:2 EtOAc/Hexane) | 3.28 | 1 | 5,6,7,8,9, 10,11 |
| 23 | 2-Cl—Ph | 4-MeO—Ph | H | isopropyl-sulfonyl | 1-(2-chlorophenyl)-5-(isopropylsulfonyl)-2-(4-methoxyphenyl)-4,5,6,7-tetrahydro-1H-pyrrolo[3,2-c]pyridine | 445 | 0.31 (1:2 EtOAc/Hexane) | 3.54 | 1 | 5,6,7,8,9, 10,11 |
| 24 | 2-Cl—Ph | 4-MeO—Ph | H | 2-fluorophenyl-sulfonyl | 1-(2-chlorophenyl)-5-[(2-fluorophenyl)sulfonyl]-2-(4-methoxyphenyl)-4,5,6,7-tetrahydro-1H-pyrrolo[3,2-c]pyridine | 497 | 0.32 (1:2 EtOAc/Hexane) | 3.77 | 1 | 5,6,7,8,9, 10,11 |
| 25 | 2-Cl—Ph | 4-MeO—Ph | H | 3-fluorophenyl-sulfonyl | 1-(2-chlorophenyl)-5-[(3-fluorophenyl)sulfonyl]-2-(4-methoxyphenyl)-4,5,6,7-tetrahydro-1H-pyrrolo[3,2-c]pyridine | 497 | 0.36 (1:2 EtOAc/Hexane) | 3.82 | 1 | 5,6,7,8,9, 10,11 |
| 26 | 2-Cl—Ph | 4-MeO—Ph | H | 4-fluorophenyl-sulfonyl | 1-(2-chlorophenyl)-5-[(4-fluorophenyl)sulfonyl]-2-(4-methoxyphenyl)-4,5,6,7-tetrahydro-1H-pyrrolo[3,2-c]pyridine | 497 | 0.39 (1:2 EtOAc/Hexane) | 3.80 | 1 | 5,6,7,8,9, 10,11 |
| 27 | 2-Cl—Ph | 4-MeO—Ph | H | (2-trifluoromethyl-phenyl)-sulfonyl | 1-(2-chlorophenyl)-2-(4-methoxyphenyl)-5{[2-(trifluoromethyl)phenyl]sulfonyl}-4,5,6,7-tetrahydro-1H-pyrrolo[3,2-c]pyridine | 547 | 0.32 (1:2 EtOAc/Hexane) | 3.91 | 1 | 5,6,7,8,9, 10,11 |
| 28 | 2-Cl—Ph | 4-MeO—Ph | H | (3-trifluoromethyl-phenyl)-sulfonyl | 1-(2-chlorophenyl)-2-(4-methoxyphenyl)-5{[3-(trifluoromethyl)phenyl]sulfonyl}-4,5,6,7-tetrahydro-1H-pyrrolo[3,2-c]pyridine | 547 | 0.38 (1:2 EtOAc/Hexane) | 3.97 | 1 | 5,6,7,8,9, 10,11 |
| 29 | 2-Cl—Ph | 4-MeO—Ph | H | (4-trifluoromethyl-phenyl)-sulfonyl | 1-(2-chlorophenyl)-2-(4-methoxyphenyl)-5{[4-(trifluoromethyl)phenyl]sulfonyl}-4,5,6,7-tetrahydro-1H-pyrrolo[3,2-c]pyridine | 547 | 0.48 (1:2 EtOAc/Hexane) | 4.01 | 1 | 5,6,7,8,9, 10,11 |
| 30 | 2-Cl—Ph | 4-MeO—Ph | H | (2-trifluoromethoxy-phenyl)-sulfonyl | 1-(2-chlorophenyl)-2-(4-methoxyphenyl)-5{[2-(trifluoromethyl)phenyl]sulfonyl}-4,5,6,7-tetrahydro-1H-pyrrolo[3,2-c]pyridine | 563 | 0.36 (1:2 EtOAc/Hexane) | 3.98 | 1 | 5,6,7,8,9, 10,11 |
| 31 | 2-Cl—Ph | 4-MeO—Ph | H | 2-trifluoromethyl-benzyl | 4-{1-(2-chlorophenyl)-5-[2-(trifluoromethyl)benzyl]-4,5,6,7-tetrahydro-1H-pyrrolo[3,2-c]pyridin-2-yl}phenyl methyl ether hydrochloride | 497 | | 2.76 | 1 | 5,6,7,8,9, 10,11 |
| 32 | 2-Cl—Ph | 4-MeO—Ph | H | cyclobutyl | 1-(2-chlorophenyl)-5-cyclobutyl-2-(4-methoxyphenyl)-4,5,6,7-tetrahydro-1H-pyrrolo[3,2-c]pyridine hydrochloride | 393 | | 2.39 | 1 | 5,6,7,8,9, 10,11 |
| 33 | 2-Cl—Ph | 4-MeO—Ph | H | 4-trifluoromethyl-benzyl | 4-{1-(2-chlorophenyl)-5-[4-(trifluoromethyl)benzyl]-4,5,6,7-tetrahydro-1H-pyrrolo[3,2-c]pyridin-2-yl}phenyl methyl ether hydrochloride | 497 | | 2.80 | 1 | 5,6,7,8,9, 10,11 |

TABLE 1-continued

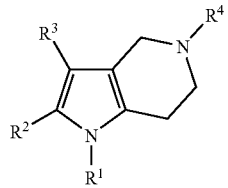

| Entry No. | R¹ | R² | R³ | R⁴ | IUPAC Name | MS m/z (MH+) | TLC Rf (solvent) | HPLC RT (min) | HPLC Method | Synthesis Method of Ex. No. |
|---|---|---|---|---|---|---|---|---|---|---|
| 34 | 2-Cl—Ph | 4-Cl—Ph | H | 4-fluoro-benzyl | 1-(2-chlorophenyl)-2-(4-chlorophenyl)-5-(4-fluorobenzyl)-4,5,6,7-tetrahydro-1H-pyrrolo[3,2-c]pyridine hydrochloride | 451 | | 2.85 | 1 | 5,6,7,8,9,10,11 |
| 35 | 2-Cl—Ph | 4-Cl—Ph | H | cyclohexyl | 1-(2-chlorophenyl)-2-(4-chlorophenyl)-5-cyclohexyl-4,5,6,7-tetrahydro-1H-pyrrolo[3,2-c]pyridine hydrochloride | 426 | | 2.83 | 1 | 5,6,7,8,9,10,11 |
| 36 | 2-Cl—Ph | 4-MeO—Ph | H | trans-4-trifluoro-methyl-cyclohexyl | trans-4-{1-(2-chlorophenyl)-5-[4-(trifluoromethyl)cyclohexyl]-4,5,6,7-tetrahydro-1H-pyrrolo[3,2-c]pyridin-2-yl}phenyl methyl ether hydrochloride | 489 | 0.35 (1:2 EtOAc/Hexane) for free amine | 2.74 | 1 | 5,6,7,8,9,10,11 |
| 37 | 2-Cl—Ph | 4-MeO—Ph | H | cis-4-trifluoro-methyl-cyclohexyl | cis-4-{1-(2-chlorophenyl)-5-[4-(trifluoromethyl)cyclohexyl]-4,5,6,7-tetrahydro-1H-pyrrolo[3,2-c]pyridin-2-yl}phenyl methyl ether hydrochloride | 489 | 0.20 (1:2 EtOAc/Hexane) for free amine | 2.77 | 1 | 5,6,7,8,9,10,11 |
| 38 | 2-Cl—Ph | 4-Cl—Ph | H | 3-trifluoro-methyl-benzyl | 1-(2-chlorophenyl)-2-(4-chlorophenyl)-5-[3-(trifluoromethyl)benzyl]-4,5,6,7-tetrahydro-1H-pyrrolo[3,2-c]pyridine hydrochloride | 501 | | 3.02 | 1 | 5,6,7,8,9,10,11 |
| 39 | 2-Cl—Ph | 4-Cl—Ph | H | 4-dime-thylamino-benzyl | N-(4-{[1-(2-chlorophenyl)-2-(4-chlorophenyl)-1,4,6,7-tetrahydro-5H-pyrrolo[3,2-c]pyridin-5-yl]methyl}phenyl)-N,N-dimethylamine dihydrochloride | 476 | | 2.86 | 1 | 5,6,7,8,9,10,11 |
| 40 | 2-Cl—Ph | 4-Cl—Ph | H | 4-trifluoro-methyl-benzyl | 1-(2-chlorophenyl)-2-(4-chlorophenyl)-5-[4-(trifluoromethyl)benzyl]-4,5,6,7-tetrahydro-1H-pyrrolo[3,2-c]pyridine hydrochloride | 501 | | 3.02 | 1 | 5,6,7,8,9,10,11 |
| 41 | 2-Cl—Ph | 4-MeO—Ph | H | 4-chlorophenyl-sulfonyl | 1-(2-chlorophenyl)-5-[(4-chlorophenyl)sulfonyl]-2-(4-methoxyphenyl)-4,5,6,7-tetrahydro-1H-pyrrolo[3,2-c]pyridine | 513 | 0.33 (1:2 EtOAc/Hexane) | 4.07 | 1 | 5,6,7,8,9,10,11 |
| 42 | 2-Cl—Ph | 4-MeO—Ph | H | 4-methyl-phenyl-sulfonyl | 1-(2-chlorophenyl)-2-(4-methoxyphenyl)-5-[(4-methylphenyl)sulfonyl]-4,5,6,7-tetrahydro-1H-pyrrolo[3,2-c]pyridine | 493 | 0.28 (1:2 EtOAc/Hexane) | 4.00 | 1 | 5,6,7,8,9,10,11 |
| 43 | 2-Cl—Ph | 4-MeO—Ph | H | 4-cyano-benzoyl | 4-{[1-(2-chlorophenyl)-2-(4-methoxyphenyl)-1,4,6,7-tetrahydro-5H-pyrrolo[3,2-c]pyridin-5-yl]carbonyl}benzonitrile | 468 | 0.09 (1:2 EtOAc/Hexane) | 3.52 | 1 | 5,6,7,8,9,10,11 |
| 44 | 2-Cl—Ph | 4-MeO—Ph | H | 4-cyano-benzyl | 4-{[1-(2-chlorophenyl)-2-(4-methoxyphenyl)-1,4,6,7-tetrahydro-5H-pyrrolo[3,2-c]pyridin-5-yl]methyl}benzonitrile | 454 | 0.06 (1:2 EtOAc/Hexane) | 2.61 | 1 | 5,6,7,8,9,10,11 |
| 45 | 2-Cl—Ph | 4-MeO—Ph | H | 4-acetamido-benzyl | N-(4-{[1-(2-chlorophenyl)-2-(4-methoxyphenyl)-1,4,6,7-tetrahydro-5H-pyrrolo[3,2-c]pyridin-5-yl]methyl}phenyl)acetamide | 486 | 0.18 (EtOAc) | 2.50 | 1 | 5,6,7,8,9,10,11 |
| 46 | 2-Cl—Ph | 4-MeO—Ph | H | 4-(1-imidazolo)-benzyl | 1-(2-chlorophenyl)-5-[4-(1H-imidazol-1-yl)benzyl]-2-(4-methoxyphenyl)-4,5,6,7-tetrahydro-1H-pyrrolo[3,2-c]pyridine | 495 | 0.08 (EtOAc) | 2.17 | 1 | 5,6,7,8,9,10,11 |
| 47 | 2-Cl—Ph | 4-MeO—Ph | H | 3-chloro-benzoyl | 5-(3-chlorobenzoyl)-1-(2-chlorophenyl)-2-(4-methoxyphenyl)-4,5,6,7-tetrahydro-1H-pyrrolo[3,2-c]pyridine | 477 | 0.19 (1:2 EtOAc/Hexane) | 3.83 | 1 | 5,6,7,8,9,10,11 |
| 48 | 2-Cl—Ph | 4-MeO—Ph | H | 4-chloro-benzoyl | 5-(4-chlorobenzoyl)-1-(2-chlorophenyl)-2-(4-methoxyphenyl)-4,5,6,7-tetrahydro-1H-pyrrolo[3,2-c]pyridine | 477 | 0.19 (1:2 EtOAc/Hexane) | 3.83 | 1 | 5,6,7,8,9,10,11 |
| 49 | 2-Cl—Ph | 4-MeO—Ph | H | 3-cyano-benzoyl | 3-{[1-(2-chlorophenyl)-2-(4-methoxyphenyl)-1,4,6,7-tetrahydro-5H-pyrrolo[3,2-c]pyridin-5-yl]carbonyl}benzonitrile | 468 | 0.09 (1:2 EtOAc/Hexane) | 3.51 | 1 | 5,6,7,8,9,10,11 |
| 50 | 2-Cl—Ph | 4-MeO—Ph | H | 3-chloro-benzyl | 4-[5-(3-chlorobenzyl)-1-(2-chlorophenyl)-4,5,6,7-tetrahydro-1H-pyrrolo[3,2-c]pyridin-2-yl]phenyl methyl ether hydrochloride | 463 | | 2.57 | 1 | 5,6,7,8,9,10,11 |

TABLE 1-continued

| Entry No. | R¹ | R² | R³ | R⁴ | IUPAC Name | MS m/z (MH+) | TLC Rf (solvent) | HPLC RT (min) | HPLC Method | Synthesis Method of Ex. No. |
|---|---|---|---|---|---|---|---|---|---|---|
| 51 | 2-Cl—Ph | 4-MeO—Ph | H | 4-chloro-benzyl | 4-[5-(4-chlorobenzyl)-1-(2-chlorophenyl)-4,5,6,7-tetrahydro-1H-pyrrolo[3,2-c]pyridin-2-yl]phenyl methyl ether hydrochloride | 463 | | 2.64 | 1 | 5,6,7,8,9,10,11 |
| 52 | 2-Cl—Ph | 4-MeO—Ph | H | 3-cyano-benzyl | 3-{[1-(2-chlorophenyl)-2-(4-methoxyphenyl)-1,4,6,7-tetrahydro-5H-pyrrolo[3,2-c]pyridin-5-yl]methyl}benzonitrile hydrochloride | 454 | | 2.43 | 1 | 5,6,7,8,9,10,11 |
| 53 | 2-Cl—Ph | 4-Cl—Ph | H | 4-fluorophenyl-sulfonyl | 1-(2-chlorophenyl)-2-(4-chlorophenyl)-5-[(4-fluorophenyl)sulfonyl]-4,5,6,7-tetrahydro-1H-pyrrolo[3,2-c]pyridine | 501 | 0.35 (5:1 Hexane/EtOAc) | 4.20 | 1 | 5,6,7,8,9,10,11 |
| 54 | 2-Cl—Ph | 4-Cl—Ph | H | 4-cyano-benzoyl | 4-{[1-(2-chlorophenyl)-2-(4-chlorophenyl)-1,4,6,7-tetrahydro-5H-pyrrolo[3,2-c]pyridin-5-yl]carbonyl}benzonitrile | 472 | 0.50 (2:1 Hexane/EtOAc) | 3.72 | 1 | 5,6,7,8,9,10,11 |
| 55 | 2-Cl—Ph | 4-Cl—Ph | H | 3-fluorophenyl-sulfonyl | 1-(2-chlorophenyl)-2-(4-chlorophenyl)-5-[(3-fluorophenyl)sulfonyl]-4,5,6,7-tetrahydro-1H-pyrrolo[3,2-c]pyridine | 501 | 0.28 (5:1 EtOAc/Hexane) | 4.22 | 1 | 5,6,7,8,9,10,11 |
| 56 | 2-Cl—Ph | 4-Cl—Ph | H | (4-trifluoro-methyl-phenyl)-sulfonyl | 1-(2-chlorophenyl)-2-(4-chlorophenyl)-5-{[4-(trifluoromethyl)phenyl]sulfonyl}-4,5,6,7-tetrahydro-1H-pyrrolo[3,2-c]pyridine | 551 | 0.32 (5:1 Hexane/EtOAc) | 4.34 | 1 | 5,6,7,8,9,10,11 |
| 57 | 2-Cl—Ph | 4-Cl—Ph | H | (3-trifluoro-methyl-phenyl)-sulfonyl | 1-(2-chlorophenyl)-2-(4-chlorophenyl)-5-{[3-(trifluoromethyl)phenyl]sulfonyl}-4,5,6,7-tetrahydro-1H-pyrrolo[3,2-c]pyridine | 551 | 0.26 (5:1 Hexane/EtOAc) | 4.32 | 1 | 5,6,7,8,9,10,11 |
| 58 | 2-Cl—Ph | 4-MeO—Ph | H | cyclohexyl | 1-(2-chlorophenyl)-5-cyclohexyl-2-(4-methoxyphenyl)-4,5,6,7-tetrahydro-1H-pyrrolo[3,2-c]pyridine | 421 | 0.15 (EtOAc) | 2.67 | 1 | 5,6,7,8,9,10,11 |
| 59 | 2-Cl—Ph | 4-MeO—Ph | H | 2-cyano-phenyl | 2-[1-(2-chlorophenyl)-2-(4-methoxyphenyl)-1,4,6,7-tetrahydro-5H-pyrrolo[3,2-c]pyridin-5-yl]benzonitrile | 440 | 0.38 (1:2 EtOAc/Hexane) | 4.12 | 1 | 5,6,7,8,9,10,11 |
| 60 | 2-Cl—Ph | 4-MeO—Ph | H | 4-cyano-phenyl | 4-[1-(2-chlorophenyl)-2-(4-methoxyphenyl)-1,4,6,7-tetrahydro-5H-pyrrolo[3,2-c]pyridin-5-yl]benzonitrile | 440 | 0.32 (1:2 EtOAc/Hexane) | 3.93 | 1 | 5,6,7,8,9,10,11 |
| 61 | 2-Cl—Ph | 4-CF3—Ph | H | 4-fluoro-benzyl | 1-(2-chlorophenyl)-5-(4-fluorobenzyl)-2-[4-(trifluoromethyl)phenyl]-4,5,6,7-tetrahydro-1H-pyrrolo[3,2-c]pyridine hydrochloride | 485 | | 2.70 | 1 | 5,6,7,8,9,10,11 |
| 62 | 2-Cl—Ph | 4-CF3—Ph | H | benzyl | 5-benzyl-1-(2-chlorophenyl)-2-[4-(trifluoromethyl)phenyl]-4,5,6,7-tetrahydro-1H-pyrrolo[3,2-c]pyridine hydrochloride | 467 | | 2.98 | 1 | 5,6,7,8,9,10,11 |
| 63 | 2-Cl—Ph | 4-CF3—Ph | H | 4-cyano-benzyl | 4-({1-(2-chlorophenyl)-2-[4-(trifluoromethyl)phenyl]-1,4,6,7-tetrahydro-5H-pyrrolo[3,2-c]pyridin-5-yl}methyl)benzonitrile hydrochloride | 492 | | 2.69 | 1 | 5,6,7,8,9,10,11 |
| 64 | 2-Cl—Ph | 4-CF3—Ph | H | 4-cyano-benzoyl | 4-({1-(2-chlorophenyl)-2-[4-(trifluoromethyl)phenyl]-1,4,6,7-tetrahydro-5H-pyrrolo[3,2-c]pyridin-5-yl}carbonyl)benzonitrile | 507 | 0.38 (3:1 Hexane/EtOAc) | 3.75 | 1 | 5,6,7,8,9,10,11 |
| 65 | 2-Cl—Ph | 4-MeO—Ph | H | 3-cyano-phenyl | 3-[1-(2-chlorophenyl)-2-(4-methoxyphenyl)-1,4,6,7-tetrahydro-5H-pyrrolo[3,2-c]pyridin-5-yl]benzonitrile | 441 | 0.36 (1:2 EtOAc/Hexane) | 3.99 | 1 | 5,6,7,8,9,10,11 |
| 66 | 2-Cl—Ph | 4-MeO—Ph | H | 4-chloro-benzyl | 5-(4-chlorobenzyl)-1-(2-chlorophenyl)-2-(4-methoxyphenyl)-4,5,6,7-tetrahydro-1H-pyrrolo[3,2-c]pyridine | 464 | 0.18 (1:1 EtOAc/Hexane) | 2.65 | 1 | 5,6,7,8,9,10,11 |
| 67 | 2-Cl—Ph | 4-MeO—Ph | H | benzyl | 5-benzyl-1-(2-chlorophenyl)-2-(4-methoxyphenyl)-4,5,6,7-tetrahydro-1H-pyrrolo[3,2-c]pyridine | 429 | 0.12 (1:1 EtOAc/Hexane) | 2.51 | 1 | 5,6,7,8,9,10,11 |
| 68 | 2-Cl—Ph | 4-MeO—Ph | H | benzyl | 5-benzyl-1-(2-chlorophenyl)-2-(4-methoxyphenyl)-4,5,6,7-tetrahydro-1H-pyrrolo[3,2-c]pyridine hydrochloride | 429 | | 2.52 | | 5,6,7,8,9,10,11 |

TABLE 1-continued

[Structure: pyrrolo[3,2-c]pyridine core with substituents R1 (on pyrrole N), R2 (on pyrrole C2), R3 (on pyrrole C3), R4 (on piperidine N)]

| Entry No. | R1 | R2 | R3 | R4 | IUPAC Name | MS m/z (MH+) | TLC Rf (solvent) | HPLC RT (min) | HPLC Method | Synthesis Method of Ex. No. |
|---|---|---|---|---|---|---|---|---|---|---|
| 69 | 2,4-Cl$_2$—Ph | 4-Cl—Ph | Me | cyclohexyl | 2-(4-chlorophenyl)-5-cyclohexyl-1-(2,4-dichlorophenyl)-3-methyl-4,5,6,7-tetrahydro-1H-pyrrolo[3,2-c]pyridine trifluoroacetate | 473 | | 3.30 | 2 | 5,6,7,8,9,10,11 |
| 70 | 2,4-Cl$_2$—Ph | 4-Cl—Ph | Me | H | 2-(4-chlorophenyl)-1-(2,4-dichlorophenyl)-3-methyl-4,5,6,7-tetrahydro-1H-pyrrolo[3,2-c]pyridine trifluoroacetate | 391 | | 2.96 | 2 | 4 |
| 71 | 2,4-Cl$_2$—Ph | 4-Cl—Ph | Me | 2-trifluoromethyl-benzyl | 2-(4-chlorophenyl)-1-(2,4-dichlorophenyl)-3-methyl-5-[2-(trifluoromethyl)benzyl]-4,5,6,7-tetrahydro-1H-pyrrolo[3,2-c]pyridine trifluoroacetate | 549 | | 3.51 | 2 | 5,6,7,8,9,10,11 |
| 72 | 2,4-Cl$_2$—Ph | 4-Cl—Ph | Me | cyclohexyl | 1-(2-chlorophenyl)-2-(4-chlorophenyl)-5-cyclohexyl-3-methyl-4,5,6,7-tetrahydro-1H-pyrrolo[3,2-c]pyridine hydrochloride | 439 | | 3.11 | 2 | 5,6,7,8,9,10,11 |
| 73 | 2-Cl—Ph | 4-Cl—Ph | Me | trans-2-hydroxy-cyclohexyl | trans-2-[1-(2-chlorophenyl)-2-(4-chlorophenyl)-3-methyl-1,4,6,7-tetrahydro-5H-pyrrolo[3,2-c]pyridin-5-yl]cyclohexanol hydrochloride | 455 | | 2.68 | 2 | 5,6,7,8,9,10,11 |
| 74 | 2-Cl—Ph | 4-Cl—Ph | Me | cyclobutyl | 1-(2-chlorophenyl)-2-(4-chlorophenyl)-5-cyclobutyl-3-methyl-4,5,6,7-tetrahydro-1H-pyrrolo[3,2-c]pyridine trifluoroacetate | 411 | | 2.96 | 2 | 5,6,7,8,9,10,11 |
| 75 | 2-Cl—Ph | 4-Cl—Ph | Me | cyclopentyl | 1-(2-chlorophenyl)-2-(4-chlorophenyl)-5-cyclopentyl-3-methyl-4,5,6,7-tetrahydro-1H-pyrrolo[3,2-c]pyridine trifluoroacetate | 425 | | 2.96 | 2 | 5,6,7,8,9,10,11 |
| 76 | 2-Cl—Ph | 4-Cl—Ph | Me | 4-trifluoromethyl-cyclohexyl | 1-(2-chlorophenyl)-2-(4-chlorophenyl)-3-methyl-5-[4-(trifluoromethyl)cyclohexyl]-4,5,6,7-tetrahydro-1H-pyrrolo[3,2-c]pyridine trifluoroacetate (cis/trans mixture) | 507 | | 3.11 | 2 | 5,6,7,8,9,10,11 |
| 77 | 2-Cl—Ph | 4-Cl—Ph | Me | 4-dimethylamino-benzyl | N-(4-{[1-(2-chlorophenyl)-2-(4-chlorophenyl)-3-methyl-1,4,6,7-tetrahydro-5H-pyrrolo[3,2-c]pyridin-5-yl]methyl}phenyl)-N,N-dimethylamine bis(trifluoroacetate) | 490 | | 3.03 | 2 | 5,6,7,8,9,10,11 |
| 78 | 2-Cl—Ph | 4-Cl—Ph | Me | 2-trifluoromethyl-benzyl | 1-(2-chlorophenyl)-2-(4-chlorophenyl)-3-methyl-5-[2-(trifluoromethyl)benzyl]-4,5,6,7-tetrahydro-1H-pyrrolo[3,2-c]pyridine trifluoroacetate | 515 | | 3.22 | 2 | 5,6,7,8,9,10,11 |
| 79 | 2-Cl—Ph | 4-Cl—Ph | Me | cyclohexyl-carbonyl | 1-(2-chlorophenyl)-2-(4-chlorophenyl)-5-(cyclohexylcarbonyl)-3-methyl-4,5,6,7-tetrahydro-1H-pyrrolo[3,2-c]pyridine | 467 | | 3.95 | 2 | 5,6,7,8,9,10,11 |
| 80 | 2-Cl—Ph | 4-Cl—Ph | Me | 1-pyrrolidinyl-carbonyl | 1-(2-chlorophenyl)-2-(4-chlorophenyl)-3-methyl-5-(1-pyrrolidinylcarbonyl)-4,5,6,7-tetrahydro-1H-pyrrolo[3,2-c]pyridine | 454 | | 3.71 | 2 | 5,6,7,8,9,10,11 |
| 81 | 2-Cl—Ph | 4-Cl—Ph | Me | (2-trifluoromethoxyphenyl)-sulfonyl | 1-(2-chlorophenyl)-2-(4-chlorophenyl)-3-methyl-5-{[2-(trifluoromethoxy)phenyl]sulfonyl}-4,5,6,7-tetrahydro-1H-pyrrolo[3,2-c]pyridine | 581 | | 4.24 | 2 | 5,6,7,8,9,10,11 |
| 82 | 2-Cl—Ph | 4-Cl—Ph | Me | 3-pyridinyl-amino-carbonyl | 1-(2-chlorophenyl)-2-(4-chlorophenyl)-3-methyl-N-(3-pyridinyl)-1,4,6,7-tetrahydro-5H-pyrrolo[3,2-c]pyridine-5-carboxamide trifluoroacetate | 477 | | 2.41 | 2 | 5,6,7,8,9,10,11 |
| 83 | 2-Cl—Ph | 4-Cl—Ph | Me | trans-2-hydroxy-cyclopentyl | trans-2-[1-(2-chlorophenyl)-2-(4-chlorophenyl)-3-methyl-1,4,6,7-tetrahydro-5H-pyrrolo[3,2-c]pyridin-5-yl]cyclopentanol | 441 | | 2.48 | 2 | 5,6,7,8,9,10,11 |
| 84 | 2-Me—Ph | 4-MeO—Ph | H | benzyl | 5-benzyl-2-(4-methoxyphenyl)-1-(2-methylphenyl)-4,5,6,7-tetrahydro-1H-pyrrolo[3,2-c]pyridine hydrochloride | 409 | | 2.30 | 2 | 5,6,7,8,9,10,11 |
| 85 | 2-Me—Ph | 4-MeO—Ph | H | trans-2-hydroxy-cyclohexyl | trans-2-[2-(4-methoxyphenyl)-1-(2-methylphenyl)-1,4,6,7-tetrahydro-5H-pyrrolo[3,2-c]pyridin-5-yl]cyclohexanol hydrochloride | 417 | | 2.34 | 2 | 5,6,7,8,9,10,11 |

TABLE 1-continued

Structure: pyrrolo[3,2-c]pyridine core with R1 on N1, R2 at 2-position, R3 at 3-position, R4 on N5.

| Entry No. | R¹ | R² | R³ | R⁴ | IUPAC Name | MS m/z (MH+) | TLC Rf (solvent) | HPLC RT (min) | HPLC Method | Synthesis Method of Ex. No. |
|---|---|---|---|---|---|---|---|---|---|---|
| 86 | 2-Me—Ph | 4-MeO—Ph | Me | benzyl | 4-[5-benzyl-3-methyl-1-(2-methylphenyl)-4,5,6,7-tetrahydro-1H-pyrrolo[3,2-c]pyridin-2-yl]phenyl methyl ether trifluoroacetate | 423 | | 2.56 | 2 | 5,6,7,8,9 10,11 |
| 87 | 2-Me—Ph | 4-MeO—Ph | Me | benzyl | 4-[5-benzyl-3-methyl-1-(2-methylphenyl)-4,5,6,7-tetrahydro-1H-pyrrolo[3,2-c]pyridin-2-yl]phenyl methyl ether hydrochloride | 423 | | 2.56 | 2 | 5,6,7,8,9 10,11 |
| 88 | 2-Me—Ph | 4-Cl—Ph | Me | benzyl | 5-benzyl-2-(4-chlorophenyl)-3-methyl-1-(2-methylphenyl)-4,5,6,7-tetrahydro-1H-pyrrolo[3,2-c]pyridine | 427 | | 2.70 | 2 | 5,6,7,8,9 10,11 |
| 89 | 2-Me—Ph | Ph | Me | benzyl | 5-benzyl-3-methyl-1-(2-methylphenyl)-2-phenyl-4,5,6,7-tetrahydro-1H-pyrrolo[3,2-c]pyridine hydrochloride | 393 | | 2.49 | 2 | 5,6,7,8,9 10,11 |
| 90 | 2-Me—Ph | 4-Cl—Ph | Me | H | 2-(4-chlorophenyl)-3-methyl-1-(2-methylphenyl)-4,5,6,7-tetrahydro-1H-pyrrolo[3,2-c]pyridine trifluoroacetate | 336 | | 2.46 | 2 | 1 |
| 91 | 2-Me—Ph | 4-Cl—Ph | Me | 4-cyano-benzoyl | 4-{[2-(4-chlorophenyl)-3-methyl-1-(2-methylphenyl)-1,4,6,7-tetrahydro-5H-prrolo[3,2-c]pyridin-5-yl]carbonyl}benzonitrile | 466 | | 3.76 | 2 | 5,6,7,8,9 10,11 |
| 92 | 2-Me—Ph | Ph | Me | 4-cyano-benzoyl | 4-{[(3-methyl-1-(2-methylphenyl)-2-phenyl-1,4,6,7-tetrahydro-5H-pyrrolo[3,2-c]pyridin-5-yl]carbonyl}benzonitrile | 432 | | 3.41 | 2 | 5,6,7,8,9 10,11 |
| 93 | 2-Me—Ph | Ph | Me | 3-trifluoro-methyl-benzoyl | 3-methyl-1-(2-methylphenyl)-2-phenyl-5-[3-(trifluoromethyl)benzoyl]-4,5,6,7-tetrahydro-1H-pyrrolo[3,2-c]pyridine | 475 | | 3.80 | 2 | 5,6,7,8,9 10,11 |
| 94 | 2-Me—Ph | 4-Cl—Ph | Me | 3-trifluoro-methyl-benzoyl | 2-(4-chlorophenyl)-3-methyl-1-(2-methylphenyl)-5-[3-(trifluoromethyl)benzoyl]-4,5,6,7-tetrahydro-1H-pyrrolo[3,2-c]pyridine | 509 | | 4.00 | 2 | 5,6,7,8,9 10,11 |
| 95 | 2-Me—Ph | 4-Cl—Ph | Me | 4-trifluoro-methoxy-benzoyl | 2-(4-chlorophenyl)-3-methyl-1-(2-methylphenyl)-5-[4-(trifluoromethoxy)benzoyl]-4,5,6,7-tetrahydro-1H-pyrrolo[3,2-c]pyridine | 525 | | 4.14 | 2 | 5,6,7,8,9 10,11 |
| 96 | 2-Me—Ph | Ph | Me | 4-trifluoro-methoxy-benzoyl | 3-methyl-1-(2-methylphenyl)-2-phenyl-5-[4-(trifluoromethoxy)benzoyl]-4,5,6,7-tetrahydro-1H-pyrrolo[3,2-c]pyridine | 491 | | 3.83 | 2 | 5,6,7,8,9 10,11 |
| 97 | 2-Me—Ph | Ph | Me | 2,4-difluoro-benzoyl | 5-(2,4-difluorobenzoyl)-3-methyl-1-(2-methylphenyl)-2-phenyl-4,5,6,7-tetrahydro-1H-pyrrolo[3,2-c]pyridine | 443 | | 3.56 | 2 | 5,6,7,8,9 10,11 |
| 98 | 2-Me—Ph | 4-Cl—Ph | Me | 2,4-difluoro-benzoyl | 2-(4-chlorophenyl)-5-(2,4-difluoro-benzoyl)-3-methyl-1-(2-methylphenyl)-4,5,6,7-tetrahydro-1H-pyrrolo[3,2-c]pyridine | 477 | | 3.82 | 2 | 5,6,7,8,9 10,11 |
| 99 | 2-Me—Ph | 4-MeO—Ph | H | cyclohexyl-amino-carbonyl | N-cyclohexyl-2-(4-methoxyphenyl)-1-(2-methylphenyl)-1,4,6,7-tetrahydro-5H-pyrrolo[3,2-c]pyridine-5-carboxamide | 444 | | 3.44 | 2 | 5,6,7,8,9 10,11 |
| 100 | 2-Me—Ph | 4-MeO—Ph | H | (2-trifluoro-methyl-phenyl)-aminocarbonyl | 2-(4-methoxyphenyl)-1-(2-methylphenyl)-N-[2-(trifluoromethyl)phenyl]-1,4,6,7-tetrahydro-5H-pyrrolo[3,2-c]pyridine-5-carboxamide | 506 | | 3.51 | 2 | 5,6,7,8,9 10,11 |
| 101 | 2-Me—Ph | 4-MeO—Ph | H | cyclohexyl-carbonyl | 5-(cyclohexylcarbonyl)-2-(4-methoxyphenyl)-1-(2-methylphenyl)-4,5,6,7-tetrahydro-1H-pyrrolo[3,2-c]pyridine | 429 | | 3.58 | 2 | 5,6,7,8,9 10,11 |
| 102 | 2-Me—Ph | 4-MeO—Ph | H | 4-dimeth-ylamino-benzoyl | 4-{[2-(4-methoxyphenyl)-1-(2-methylphenyl)-1,4,6,7-tetrahydro-5H-pyrrolo[3,2-c]pyridin-5-yl]carbonyl}-N,N-dimethylaniline hydrochloride | 466 | | 3.26 | 2 | 5,6,7,8,9 10,11 |
| 103 | 2-Me—Ph | 4-MeO—Ph | H | 2-trifluoro-methyl-benzoyl | 2-(4-methoxyphenyl)-1-(2-methylphenyl)-5-[2-(trifluoromethyl)benzoyl]-4,5,6,7-tetrahydro-1H-pyrrolo[3,2-c]pyridine | 492 | | 3.51 | 2 | 5,6,7,8,9 10,11 |
| 104 | 2-Me—Ph | 4-MeO—Ph | H | 1,3-benzodioxol-5-yl-carbonyl | 5-(1,3-benzodioxol-5-ylcarbonyl)-2-(4-methoxyphenyl)-1-(2-methylphenyl)-4,5,6,7-tetrahydro-1H-pyrrolo[3,2-c]pyridine | 468 | | 3.33 | 2 | 5,6,7,8,9 10,11 |

TABLE 1-continued

| Entry No. | R¹ | R² | R³ | R⁴ | IUPAC Name | MS m/z (MH+) | TLC Rf (solvent) | HPLC RT (min) | HPLC Method | Synthesis Method of Ex. No. |
|---|---|---|---|---|---|---|---|---|---|---|
| 105 | 2-Me—Ph | 4-MeO—Ph | H | 4-trifluoromethoxy-benzoyl | 2-(4-methoxyphenyl)-1-(2-methylphenyl)-5-[4-(trifluoromethoxy)benzoyl]-4,5,6,7-tetrahydro-1H-pyrrolo[3,2-c]pyridine | 508 | | 3.69 | 2 | 5,6,7,8,9 10,11 |
| 106 | 2-Me—Ph | 4-MeO—Ph | H | (1-methyl-cyclohexyl)-carbonyl | 2-(4-methoxyphenyl)-5-[(1-methylcyclohexyl)carbonyl]-1-(2-methylphenyl)-4,5,6,7-tetrahydro-1H-pyrrolo[3,2-c]pyridine | 444 | | 3.95 | 2 | 5,6,7,8,9 10,11 |
| 107 | 2-Me—Ph | 4-MeO—Ph | H | phenyl-sulfonyl | 2-(4-methoxyphenyl)-1-(2-methylphenyl)-5-(phenylsulfonyl)-4,5,6,7-tetrahydro-1H-pyrrolo[3,2-c]pyridine | 460 | | 3.68 | 2 | 5,6,7,8,9 10,11 |
| 108 | 2-Me—Ph | 4-MeO—Ph | H | cyclohexyl | 5-cyclohexyl-2-(4-methoxyphenyl)-1-(2-methylphenyl)-4,5,6,7-tetrahydro-1H-pyrrolo[3,2-c]pyridine | 402 | | 2.45 | 2 | 5,6,7,8,9 10,11 |
| 109 | 2-Me—Ph | 4-MeO—Ph | H | cyclohexyl | 5-cyclohexyl-2-(4-methoxyphenyl)-1-(2-methylphenyl)-4,5,6,7-tetrahydro-1H-pyrrolo[3,2-c]pyridine hydrochloride | 402 | | 2.45 | 2 | 5,6,7,8,9 10,11 |
| 110 | 2-Me—Ph | 4-MeO—Ph | H | 1-benzyl-4-piperidinyl | 5-(1-benzyl-4-piperidinyl)-2-(4-methoxyphenyl)-1-(2-methylphenyl)-4,5,6,7-tetrahydro-1H-pyrrolo[3,2-c]pyridine | 493 | | 1.95 | 2 | 5,6,7,8,9 10,11 |
| 111 | 2-Me—Ph | 4-MeO—Ph | H | 4-dimethylamino-benzyl | 4{[2-(4-methoxyphenyl)-1-(2-methylphenyl)-1,4,6,7-tetrahydro-5H-pyrrolo[3,2-c]pyridin-5-yl]methyl}-N,N-dimethylaniline | 453 | | 2.83 | 2 | 5,6,7,8,9 10,11 |
| 112 | 2-Me—Ph | 4-MeO—Ph | H | 4-trifluoromethyl-benzyl | 2-(4-methoxyphenyl)-1-(2-methylphenyl)-5-[4-(trifluoromethyl)benzyl]-4,5,6,7-tetrahydro-1H-pyrrolo[3,2-c]pyridine | 478 | | 2.56 | 2 | 5,6,7,8,9 10,11 |
| 113 | 2-Me—Ph | 4-MeO—Ph | H | 2-trifluoromethyl-benzyl | 2-(4-methoxyphenyl)-1-(2-methylphenyl)-5-[2-(trifluoromethyl)benzyl]-4,5,6,7-tetrahydro-1H-pyrrolo[3,2-c]pyridine | 478 | | 2.63 | 2 | 5,6,7,8,9 10,11 |
| 114 | 2-Me—Ph | 4-MeO—Ph | H | 4-(1-pyrrolidiny benzyl | 2-(4-methoxyphenyl)-1-(2-methylphenyl)-5-[4-(1-pyrrolidinyl)benzyl]-4,5,6,7-tetrahydro-1H-pyrrolo[3,2-c]pyridine | 479 | | 2.69 | 2 | 5,6,7,8,9 10,11 |
| 115 | 2-Me—Ph | 4-MeO—Ph | Me | cyclohexyl | 5-cyclohexyl-2-(4-methoxyphenyl)-3-methyl-1-(2-methylphenyl)-4,5,6,7-tetrahydro-1H-pyrrolo[3,2-c]pyridine hydrochloride | 416 | | 2.52 | 2 | 5,6,7,8,9 10,11 |
| 116 | 2-Me—Ph | 4-MeO—Ph | Me | 4-dimethylamino-benzyl | 4{[2-(4-methoxyphenyl)-3-methyl-1-(2-methylphenyl)-1,4,6,7-tetrahydro-5H-pyrrolo[3,2-c]pyridin-5-yl]methyl}-N,N-dimethylaniline dihydrochloride | 467 | | 2.52 | 2 | 5,6,7,8,9 10,11 |
| 117 | 2-Me—Ph | 4-MeO—Ph | Me | 3-trifluoromethyl-benzyl | 2-(4-methoxyphenyl)-3-methyl-1-(2-methylphenyl)-5-[3-(trifluoromethyl)benzyl]-4,5,6,7-tetrahydro-1H-pyrrolo[3,2-c]pyridine hydrochloride | 492 | | 2.63 | 2 | 5,6,7,8,9 10,11 |
| 118 | 2-Me—Ph | 4-MeO—Ph | Me | 4-methylsulfonyl-benzyl | 2-(4-methoxyphenyl)-3-methyl-1-(2-methylphenyl)-5-[4-(methylsulfonyl)benzyl]-4,5,6,7-tetrahydro-1H-pyrrolo[3,2-c]pyridine hydrochloride | 502 | | 2.35 | 2 | 5,6,7,8,9 10,11 |
| 119 | 2-Me—Ph | 4-MeO—Ph | Me | cyclohexyl-amino-carbonyl | N-cyclohexyl-2-(4-methoxyphenyl)-3-methyl-1-(2-methylphenyl)-1,4,6,7-tetrahydro-5H-pyrrolo[3,2-c]pyridine-5-carboxamide | 459 | | 3.56 | 2 | 5,6,7,8,9 10,11 |
| 120 | 2-Me—Ph | 4-MeO—Ph | Me | (2-methoxyphenyl)-amino-carbonyl | N-(2-methoxyphenyl)-2-(4-methoxyphenyl)-3-methyl-1-(2-methylphenyl)-1,4,6,7-tetrahydro-5H-pyrrolo[3,2-c]pyridine-5-carboxamide | 483 | | 3.61 | 2 | 5,6,7,8,9 10,11 |
| 121 | 2-Me—Ph | 4-MeO—Ph | Me | cyclohexyl-carbonyl | 5-(cyclohexylcarbonyl)-2-(4-methoxyphenyl)-3-methyl-1-(2-methylphenyl)-4,5,6,7-tetrahydro-1H-pyrrolo[3,2-c]pyridine | 444 | | 3.80 | 2 | 5,6,7,8,9 10,11 |
| 122 | 2-Me—Ph | 4-MeO—Ph | Me | isonicotinoyl | 5-isonicotinoyl-2-(4-methoxyphenyl)-3-methyl-1-(2-methylphenyl)-4,5,6,7-tetrahydro-1H-pyrrolo[3,2-c]pyridine hydrochloride | 439 | | 2.75 | 2 | 5,6,7,8,9 10,11 |

TABLE 1-continued

| Entry No. | R¹ | R² | R³ | R⁴ | IUPAC Name | MS m/z (MH+) | TLC Rf (solvent) | HPLC RT (min) | HPLC Method | Synthesis Method of Ex. No. |
|---|---|---|---|---|---|---|---|---|---|---|
| 123 | 2-Me—Ph | 4-MeO—Ph | Me | (5-dimethylaminonaphthalene)-sulfonyl | 5-{[2-(4-methoxyphenyl)-3-methyl-1-(2-methylphenyl)-1,4,6,7-tetrahydro-5H-pyrrolo[3,2-c]pyridin-5-yl]sulfonyl}-N,N-dimethyl-1-naphthalenamine hydrochloride | 567 | | 3.95 | 2 | 5,6,7,8,9 10,11 |
| 124 | 2-Me—Ph | 4-MeO—Ph | Me | trans-2-hydroxycyclohexyl | trans-2-[2-(4-methoxyphenyl)-3-methyl-1-(2-methylphenyl)-1,4,6,7-tetrahydro-5H-pyrrolo[3,2-c]pyridin-5-yl]cyclohexanol hydrochloride | 432 | | 2.30 | 2 | 5,6,7,8,9 10,11 |
| 125 | 2-Me—Ph | 4-MeO—Ph | H | H | 2-(4-methoxyphenyl)-1-(2-methylphenyl) 4,5,6,7-tetrahydro-1H-pyrrolo[3,2-c]pyridine | 432 | | 2.11 | 2 | 1 |
| 126 | 2-Me—Ph | 4-MeO—Ph | H | 3-trifluoromethyl-benzyl | methyl 4-{1-(2-methylphenyl)-5-[3-(trifluoromethyl)benzyl]-4,5,6,7-tetrahydro-1H-pyrrolo[3,2-c]pyridin-2-yl}phenyl ether hydrochloride | 478 | | 2.46 | 2 | 5,6,7,8,9 10,11 |
| 127 | 2-Me—Ph | 4-MeO—Ph | Me | 4-trifluoromethyl-benzyl | 2-(4-methoxyphenyl)-3-methyl-1-(2-methylphenyl)-5-[4-(trifluoromethyl)benzyl]-4,5,6,7-tetrahydro-1H-pyrrolo[3,2-c]pyridine hydrochloride | 492 | | 2.61 | 2 | 5,6,7,8,9 10,11 |
| 128 | 2-Cl—Ph | 4-Cl—Ph | Me | (R,R)-2-hydroxycyclohexyl | (R,R)-2-[1-(2-chlorophenyl)-2-(4-chlorophenyl)-3-methyl-1,4,6,7-tetrahydro-5H-pyrrolo[3,2-c]pyridin-5-yl]cyclohexanol | 456 | | 2.70 | 2 | 5,6,7,8,9 10,11 |
| 129 | 2-Cl—Ph | 4-Cl—Ph | Me | (S,S)-2-hydroxycyclohexyl | (S,S)-2-[1-(2-chlorophenyl)-2-(4-chlorophenyl)-3-methyl-1,4,6,7-tetrahydro-5H-pyrrolo[3,2-c]pyridin-5-yl]cyclohexanol | 456 | | 2.70 | 2 | 5,6,7,8,9 10,11 |
| 130 | 2-Cl—Ph | 4-Cl—Ph | Me | cis-2-hydroxycyclohexyl | cis-2-[1-(2-chlorophenyl)-2-(4-chlorophenyl)-3-methyl-1,4,6,7-tetrahydro-5H-pyrrolo[3,2-c]pyridin-5-yl]cyclohexanol | 456 | | 2.74 | 2 | 5,6,7,8,9 10,11 |
| 131 | 2-Cl—Ph | 4-MeO—Ph | H | 3-(2-furylmethoxy)-2-hydroxy-1-propyl | 1-[1-(2-chlorophenyt)-2-(4-methoxyphenyl)-1,4,6,7-tetrahydro-5H-pyrrolo[3,2-c]pyridin-5-yl]-3-(2-furylmethoxy)-2-propanol hydrochloride | 493 | | 2.30 | 2 | 5,6,7,8,9 10,11 |
| 132 | 2-Cl—Ph | 4-MeO—Ph | H | 3-butoxy-2-hydroxy-1-propyl | 1-butoxy-3-[1-(2-chlorophenyl)-2-(4-methoxyphenyl)-1,4,6,7-tetrahydro-5H-pyrrolo[3,2-c]pyridin-5-yl]-2-propanol hydrochloride | 469 | | 2.41 | 2 | 5,6,7,8,9 10,11 |
| 133 | 2-Cl—Ph | 4-MeO—Ph | H | (2S)-3-benzyloxy-2-hydroxy-1-propyl | (2S)-1-(benzyloxy)-3-[1-(2-chlorophenyl) 2-(4-methoxyphenyl)-1,4,6,7-tetrahydro-5H-pyrrolo[3,2-c]pyridin-5-yl]-2-propanol hydrochloride | 503 | | 2.52 | 2 | 5,6,7,8,9 10,11 |
| 134 | 2-Cl—Ph | 4-MeO—Ph | H | 3-[3-(trifluoromethyl)-2-pyridinyl]oxy-2-hydroxy-1-propyl | 1-[1-(2-chlorophenyl)-2-(4-methoxyphenyl)-1,4,6,7-tetrahydro-5H-pyrrolo[3,2-c]pyridin-5-yl]-3-{3-(trifluoromethyl)-2-pyridinyl]oxy-2-propanol dihydrochloride | 558 | | 2.41 | 2 | 5,6,7,8,9 10,11 |
| 135 | 2-Cl—Ph | 4-MeO—Ph | H | (2R)-3-(2-chlorophenoxy)-2-hydroxy-1-propyl | (2R)-1-(2-chlorophenyl)-3-[1-(2-chlorophenyl)-2-(4-methoxyphenyl) 1,4,6,7-tetrahydro-5H-pyrrolo[3,2-c]pyridin-5-yl]-2-propanol hydrochloride | 523 | | 3.63 | 2 | 5,6,7,8,9 10,11 |

Example 12

Preparation of methyl N-(1-piperidinyl)-β-alaninate

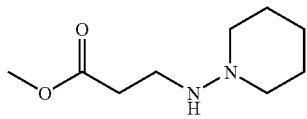

To a solution of 1-aminopiperidine (100 g, 1.00 mol) in dry MeOH (1.00 L) at 0° C., methyl acrylate (99 mL, 1.10 mol) was added dropwise over 2 h. The resulting mixture was stirred overnight at rt. The solvents were evaporated, hexane was added to the residue, and white solid (impurity) was precipitated. The solid was removed by filtration, and the filtrate was evaporated to give 94.10 g (50.5%) of the desired material as a yellow oil, which was used without purification in Example 13.

Example 13

Preparation of methyl N-(3-ethoxy-3-oxopropanoyl)-N-(1-piperidinyl)-β-alaninate

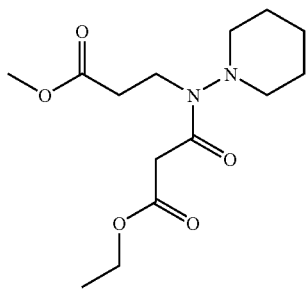

To a solution of methyl N-(1-piperidinyl)-β-alaninate (94.10 g, 505.9 mmol) in $CH_2Cl_2$ (1.00 L) and $Et_3N$ (84.45 mL, 607.1 mmol) at 0° C. was slowly added over 2 h ethyl malonyl chloride (70.98 mL, 556.5 mmol). The resulting slurry was stirred at rt for 4 h. The final color was yellow. Water was added and phases separated. The organic phases were dried over $MgSO_4$, and evaporated. The residue was purified by flash chromatography using a gradient of 9:1 to 1:1 toluene/EtOAc, to give the desired product as a yellow oil (102 g, 67%), which was used without purification in Example 14.

Example 14

Preparation of ethyl 2,4-dioxo-1,1'-bipiperidine-3-carboxylate

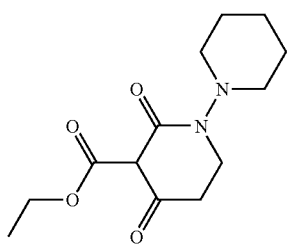

To a solution of methyl N-(3-ethoxy-3-oxopropanoyl)-N-(1-piperidinyl)-β-alaninate (43 g, 143 mmol) in a mixture of THF (2.26 L) and DMF (1.00 L) was added $Cs_2CO_3$ (140 g, 430 mmol). The resulting mixture was heated at reflux (77° C.) for 48 h. The cooled reaction was filtered, and the filtrate was evaporated. The filtrate residue and filtered solid were combined and purified by flash chromatography using 7:3 $CH_2Cl_2$/MeOH as eluant, to give 11.36 g of partially pure title material. LC-MS m/z 269.19 ($MH^+$), retention time 2.20 min (method 2).

Example 15

Preparation of 1,1'-bipiperidine-2,4-dione

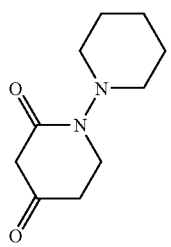

Ethyl 2,4-dioxo-1,1'-bipiperidine-3-carboxylate (11.36 g, 42.38 mmol, Example 14) was dissolved in 10% AcOH (200 mL) and heated at reflux 125° C. for 1 h. The cooled reaction was evaporated, and the residue was purified by flash chromatography using a gradient of 9:1 to 1:1 $CH_2Cl_2$/acetone, to give the product as a yellow viscous oil (6.4 g, 22% yield for the two last steps).

Example 16

Preparation of 1-(2,4-dichlorophenyl)-3-methyl-5-(1-piperidinyl)-1,5,6,7-tetrahydro-4H-pyrrolo[3,2-c]pyridin-4-one

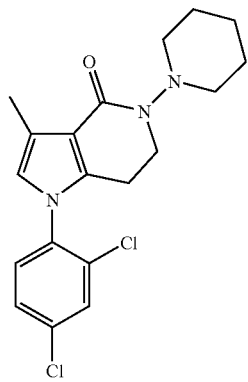

To a solution of 1,1'-bipiperidine-2,4-dione (Example 15) (260 mg, 1.32 mmol) in dry toluene (25 mL) at rt were added 1-[(2,4-dichlorophenyl)amino]acetone (288 mg, 1.32 mmol, prepared in a similar manner to Example 25) followed by p-TSA (p-toluenesulfonic acid) (25 mg, 0.132 mmol). The mixture was heated at reflux with a Dean-Stark trap, and 10 mL toluene was collected in the trap. Then, 1 equiv. of p-TSA (250 mg, 1.32 mmol) was added and the reaction mixture was heated at reflux for 6 h. The cooled reaction was evaporated and the residue purified by flash chromatography using 9:1 CH$_2$Cl$_2$/MeOH as eluant to give the title material as brown solid (215 mg, 43% yield), which was used in Example 18.

Example 17

Preparation of 5-cyclohexyl-1-(2,4-dichlorophenyl)-3-methyl-1,5,6,7-tetrahydro-4H-pyrrolo[3,2-c]pyridin-4-one

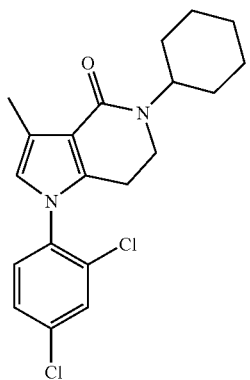

A mixture of 1-[(2,4-dichlorophenyl)amino)acetone (0.56 g, 2.561 mmol, prepared in a similar manner to Example 25), 1,1'-bipiperidine-2,4-dione (0.50 g, 2.561 mmol, Example 15), p-toluenesulfonic acid monohydrate (48.7 mg, 0.256 mmol) and toluene (5 mL) was heated at reflux for 24 h, using a Dean-Stark trap. Water that formed was collected in the trap. Evaporation of volatiles provided the crude product, which was purified on silica gel eluting with 1:7 to 1:2 EtOAc/hexanes, to give the purified product as a solid (75.0 mg, 8%): R$_f$=0.14 (1:2 EtOAc/hexanes).

Example 18

Preparation of 2-bromo-1-(2,4-dichlorophenyl)-3-methyl-5-(1-piperidinyl)-1,5,6,7-tetrahydro-4H-pyrrolo[3,2-c]pyridin-4-one

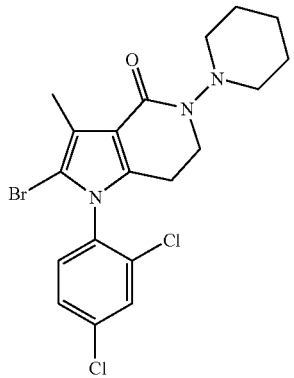

To a solution of 1-(2,4-dichlorophenyl)-3-methyl-5-(1-piperidinyl)-1,5,6,7-tetrahydro-4H-pyrrolo[3,2-c]pyridin-4-one (200 mg, 0.529 mmol, Example 16) at 0° C. in dry DMF was added NBS (N-bromosuccinimide) (99 mg, 0.555 mmol). The reaction mixture was stirred 1 h at 0° C., and then water was added. The resulting solution was extracted several times with Et$_2$O, the combined organic extracts were dried over MgSO$_4$ and evaporated. The residue was dissolved in CH$_2$Cl$_2$ and filtered through a pad of silica gel to give the title material (180 mg, 75% yield) as an orange solid, which was used in Example 19.

Example 19

Preparation of 2-(4-chlorophenyl)-1-(2,4-dichlorophenyl)-3-methyl-5-(1-piperidinyl-1,5,6,7-tetrahydro-4H-pyrrolo[3,2-c]pyridin-4-one

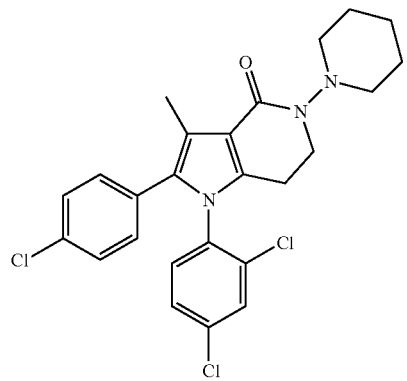

2-Bromo-1-(2,4-dichlorophenyl)-3-methyl-5-piperidinyl)-1,5,6,7-tetrahydro-4H-pyrrolo{3,2-c]pyridin-4-one (593 mg, 1.29 mmol, Example 18), 4-chloroboronic acid (223 mg, 1.42 mmol), and Pd(PPh$_3$)$_4$ (149 mg, 0.129 mmol), were dissolved in DME (27 mL) and Na$_2$CO$_3$ (1M solution, 6.45 mL). The resulting solution was degassed several times, then the flask was filled with argon and heated overnight at 60° C. Solvents were then evaporated, water and EtOAc were added, and the organic layer was separated, dried over MgSO$_4$, and evaporated. The crude material was purified by reversed phase chromatography using a gradient of 50 to 80% water/CH$_3$CN containing 0.01% TFA. The solvents were evaporated, the residue was dissolved in CH$_2$Cl$_2$, and extracted with a saturated aqueous solution of NaHCO$_3$. The organic layer was dried over MgSO$_4$, and evaporated to give 300 mg (48% yield) of the title compound as a white solid. LC-MS m/z (MH$^+$) 490, retention time 4.06 min (method 2).

Example 20

Preparation of 2-(4-chlorophenyl)-1-(3,4'-dichloro-1,1'-biphenyl-4-yl)-3-methyl-5-(1-piperidinyl)-1,5,6,7-tetrahydro-4H-pyrrolo[3,2-c]pyridin-4-one

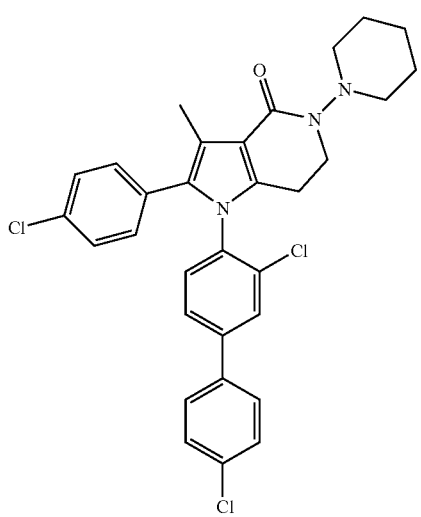

2-Bromo-1-(2,4-dichlorophenyl)-3-methyl-5-(1-piperidinyl)-1,5,6,7-tetrahydro-4H-pyrrolo[3,2-c]pyridin-4-one (213 mg, 0.466 mmol), 4-chlorophenyl boronic acid (109 mg, 0.699 mmol), and Pd(PPh3)4 (54 mg, 0.0466 mmol), were dissolved in 1,4-dioxane (10 mL) and Na$_2$CO$_3$ (1 M solution, 2.33 mL). The resulting solution was degassed several times, then the flask was filled with argon and heated overnight at reflux. Solvents were evaporated, water and EtOAc were added, phases separated, and the organic layer separated, dried over MgSO$_4$, and evaporated. The crude material was purified by flash chromatography using 9:1 CH$_2$Cl$_2$/MeOH as eluant. Fractions containing the desired material were combined, evaporated, and further purified by reversed phase chromatography using a gradient of 10 to 100% CH$_3$CN/water containing 0.01% TFA. The HPLC solvents were evaporated to give (a) the mono-alkylated compound TFA salt (6.1 mg, 2.6% yield) as a white solid, LC-MS m/z (MH$^+$) 490, retention time 4.06 min (method 2); and (b) the bis-alkylated compound TFA salt, 2-4-chlorophenyl)-1-(3,4'-dichloro-1,1'-biphenyl-4-yl)-3-methyl-5-(1-piperidinyl)-1,5,6,7-tetrahydro-4H-pyrrolo[3,2-c]pyridin-4-one trifluoroacetate, (9.4 mg, 7.1% yield) as a white solid, LC-MS m/z (MH$^+$) 566, retention time 4.43 min (method 2). The latter compound was dissolved in CH$_2$Cl$_2$ and treated with excess (10 equiv.) 2N HCl in Et$_2$O. The resulting mixture was stirred 10 minutes, then evaporated to give the final compound as HCl salt [2-(4-chlorophenyl)-1-(3,4'-dichloro-1,1'-biphenyl-4-yl)-3-methyl-5-(1-piperidinyl)-1,5,6,7-tetrahydro-4H-pyrrolo[3,2-c]pyridin-4-one hydrochloride.

Example 21

Preparation of 1-(2-chlorophenyl)-5-[(1S,2S)-2-hydroxycyclohexyl]-2-(4-methoxyphenyl)-3-methyl-1,5,6,7-tetrahydro-4H-pyrrolo[3,2-c]pyridin-4-one

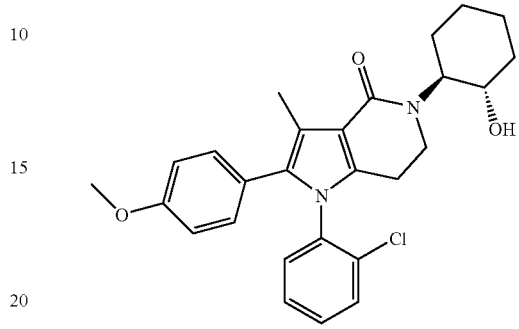

The starting material for this example, namely 5-[(1S,2S)-2-(benzyloxy)cyclohexyl]-1-(2-chlorophenyl)-2-(4-methoxyphenyl)-3-methyl-1,5,6,7-tetrahydro-4H-pyrrolo[3,2-c]pyridin-4-one, was prepared by following the methods described in Scheme 2 and Examples 12–19, using (1S,2S)-2-(benzyloxy)cyclohexylamine as R$^4$NH$_2$ (Scheme 2). Then, a sample of 5-[(1S,2S)-2-(benzyloxy)cyclohexyl]-1-(2-chlorophenyl)-2-(4-methoxyphenyl)-3-methyl-1,5,6,7-tetrahydro-4H-pyrrolo[3,2-c]pyridin-4-one (200 mg, 0.36 mmol) was dissolved in methylene chloride (5 mL). Trimethylsilyl iodide (0.054 mL, 0.396 mmol) was added dropwise and the solution was stirred at rt for 18 h. The solvent was removed and the crude material was purified by silica gel column, eluting with methylene chloride followed by methanol. The product was isolated as a white solid (40.0 mg, 24%). LC-MS m/z (MH$^+$) 465.3, retention time 3.23 min (method 1).

Example 22

Preparation of 2-(4-chlorophenyl)-1-(2,4-dichlorophenyl)-3-methyl-1,5,6,7-tetrahydro-4H-pyrrolo[3,2-c]pyridin-4-one

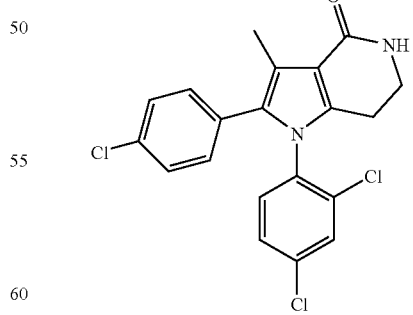

A solution of 2-(4-chlorophenyl)-1-(2,4-dichlorophenyl)-5-(2,4-dimethoxybenzyl)-3-methyl-1,5,6,7-tetrahydro-4H-pyrrolo[3,2-c]pyridin-4-one (1.13 g, 2.03 mmol, Table 2, entry 176) in trifluoroacetic acid (40 mL) was heated at reflux temperature for 2 h. Trifluoroacetic acid was removed by evaporation under reduced pressure, and the residue was purified by silica gel chromatography. Elution first with 50% ethyl acetate in hexane followed by ethyl acetate gave a yellow solid (600 mg, 73%). LC-MS m/z (MH⁺) 405.0, retention time 3.84 min (method 2).

Example 23

Preparation of 2-(4-chlorophenyl)-1-(2,4-dichlorophenyl)-3-methyl-5-(2-pyridinyl-1,5,6,7-tetrahydro-4H-pyrrolo[3,2-c]pyridin-4-one

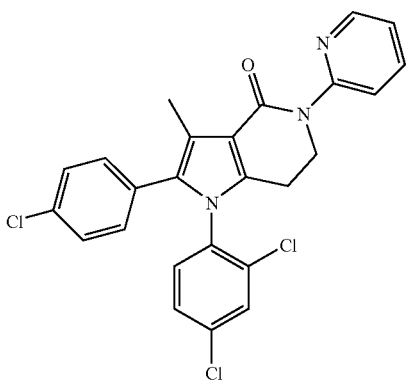

A solution of 2-(4-chlorophenyl)-1-(2,4-dichlorophenyl)-3-methyl-1,5,6,7-tetrahydro-4H-pyrrolo[3,2-c]pyridin-4-one (100 mg, 0.246 mmol, Example 22) and potassium hydride (50 mg, 1.25 mmol) in 2-bromopyridine (5 mL) was heated at 100° C. for 3 h. 2-Bromopyridine was removed by evaporation under reduced pressure, and the residue was purified by HPLC. The product (11.0 mg, 9.2%) was obtained as a TFA salt. LC-MS m/z (MH⁺) 482.1, retention time 4.28 min (method 2).

Example 24

Preparation of 1-(2-chlorophenyl)-2-(4-chlorophenyl)-3-methyl-5-(4-piperidinyl)-1,5,6,7-tetrahydro-4H-pyrrolo[3,2-c]pyridin-4-one

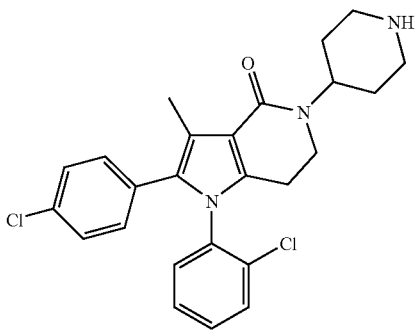

To a solution of 5-(1-benzyl-4-piperidinyl)-1-(2-chlorophenyl)-2-(4-chlorophenyl)-3-methyl-1,5,6,7-tetrahydro-4H-pyrrolo[3,2-]pyridin-4-one (178 mg, 0.327 mmol, Table 2, entry 185) in 1,2-dichloroethane (5 mL) at rt was added chloroethylchloroformate (71 μL, 0.654 mmol). The resulting mixture was heated at reflux for 3 h. The cooled reaction mixture was evaporated, and then the residue was dissolved in MeOH and heated at reflux for 2 h. Solvents were evaporated, and the residue was purified by reversed phase chromatography using a gradient of 20–60% CH₃CN/water containing 0.01% TFA, to give the title compound 1-(2-chlorophenyl)-2-(4-chlorophenyl)-3-methyl-5-(4-piperidinyl)-1,5,6,7-tetrahydro-4H-pyrrolo[3,2-c]pyridin-4-one TFA salt as a yellow solid (29 mg, 20% yield); LC-MS m/z (MH⁺) 454, retention time 2.74 min (method 2).

Example 25

Preparation of 1-[(2-chlorophenyl)amino]acetone

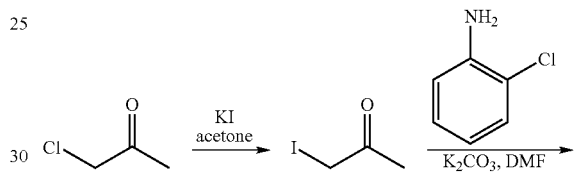

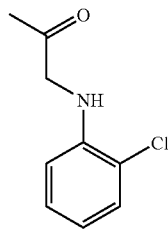

To a solution of chloroacetone (8.0 mL, 0.100 mol) in 100 mL acetone was added KI (33.20 g, 0.200 mol). The suspension was stirred under argon at rt for 24 h. Acetone was evaporated under reduced pressure. The residue was extracted with ether. The ethereal solution was concentrated under reduced pressure to yield iodoacetone as a brown liquid (18.00 g, 98%). A mixture of 2-chloroaniline (8.95 mL, 0.085 mol), iodoacetone (18.00 g, 0.098 mol), K₂CO₃ (12.35 g, 0.090 mol) and DMF (200 mL) was heated under argon for 48 h. The mixture was cooled to rt, and water was added. The mixture was extracted with ether (3×300 mL). The combined organic phases were washed with water (2×300 mL), dried over Na₂SO₄, and evaporated. The crude product was purified on silica gel, eluting with 1:5 EtOAc/hexanes to yield the product as a brown liquid (14.07 g, 77%), which was used in procedures similar to Examples 16 and 17.

Using appropriate starting materials and the experimental procedures described above for Examples 12–25, compounds appearing in Table 2 were similarly prepared.

TABLE 2

[Structure: core scaffold with R¹ on N, R² at 2-position, R³ at 3-position, R⁴ on other N, with C=O]

| Entry No. | R¹ | R² | R³ | R⁴ | IUPAC Name | MS m/z (MH+) | TLC Rf (solvent) | HPLC ret. time (LC-MS) | HPLC method | Synthesis Method of Ex. No. |
|---|---|---|---|---|---|---|---|---|---|---|
| 136 | 4-Cl—Ph | H | Me | cyclohexyl | 1-(4-chlorophenyl)-5-cyclohexyl-3-methyl-1,5,6,7-tetrahydro-4H-pyrrolo[3,2-c]pyridin-4-one | 343 | 0.31(1:1 EtOAc/Hexane) | 3.40 | 1 | 16, 17 |
| 137 | 4-Cl—Ph | Br | Me | cyclohexyl | 2-bromo-1-(4-chlorophenyl)-5-cyclohexyl-3-methyl-1,5,6,7-tetrahydro-4H-pyrrolo[3,2-c]pyridin-4-one | 421 | 0.30(1:2 EtOAc/Hexane) | 3.68 | 1 | 18 |
| 138 | 4-Cl—Ph | 4-Cl—Ph | Me | cyclohexyl | 1,2-bis(4-chlorophenyl)-5-cyclohexyl-3-methyl-1,5,6,7-tetrahydro-4H-pyrrolo[3,2-c]pyridin-4-one | 453 | 0.43(1:2 EtOAc/Hexane) | 4.27 | 1 | 19, 20 |
| 139 | 4-Cl—Ph | 2,4-Cl₂—Ph | Me | cyclohexyl | 1-(4-chlorophenyl)-5-cyclohexyl-2-(2,4-dichlorophenyl)-3-methyl-1,5,6,7-tetrahydro-4H-pyrrolo[3,2-c]pyridin-4-one | 487 | 0.40(1:2 EtOAc/Hexane) | 4.36 | 1 | 19, 20 |
| 140 | 2,4-Cl₂—Ph | 4-Cl—Ph | Me | cyclohexyl | 2-(4-chlorophenyl)-5-cyclohexyl-1-(2,4-dichlorophenyl)-3-methyl-1,5,6,7-tetrahydro-4H-pyrrolo[3,2-c]pyridin-4-one | 487 | 0.41(1:2 EtOAc/Hexane) | 4.42 | 1 | 19, 20 |
| 141 | 2,4-Cl₂—Ph | H | Me | cyclohexyl | 5-cyclohexyl-1-(2,4-dichlorophenyl)-3-methyl-1,5,6,7-tetrahydro-4H-pyrrolo[3,2-c]pyridin-4-one | 377 | 0.36(1:2 EtOAc/Hexane) | 3.76 | 1 | 16, 17 |
| 142 | 2,4-Cl₂—Ph | Br | Me | cyclohexyl | 2-bromo-5-cyclohexyl-1-(2,4-dichlorophenyl)-3-methyl-1,5,6,7-tetrahydro-4H-pyrrolo[3,2-c]pyridin-4-one | 455 | 0.45(1:2 EtOAc/Hexane) | 4.00 | 1 | 18 |
| 143 | 2,4-Cl₂—Ph | Me | H | cyclohexyl | 5-cyclohexyl-1-(2,4-dichlorophenyl)-2-methyl-1,5,6,7-tetrahydro-4H-pyrrolo[3,2-c]pyridin-4-one | 377 | 0.14(1:2 EtOAc/Hexane) | 3.57 | 1 | 16, 17 |
| 144 | 2,4-Cl₂—Ph | 4-MeO—Ph | Me | cyclohexyl | 5-cyclohexyl-1-(2,4-dichlorophenyl)-2-[4-(methylsulfanyl)phenyl]-1,5,6,7-tetrahydro-4H-pyrrolo[3,2-c]pyridin-4-one | 497 | | 3.65 | 1 | 19, 20 |
| 145 | 2,4-Cl₂—Ph | 4-vinyl-Ph | Me | cyclohexyl | 5-cyclohexyl-1-(2,4-dichlorophenyl)-2-(4-vinylphenyl)-1,5,6,7-tetrahydro-4H-pyrrolo[3,2-c]pyridin-4-one | 479 | | 4.34 | 1 | 19, 20 |
| 146 | 2,4-Cl₂—Ph | 3-thienyl | Me | cyclohexyl | 5-cyclohexyl-1-(2,4-dichlorophenyl)-3-methyl-2-(3-thienyl)-1,5,6,7-tetrahydro-4H-pyrrolo[3,2-c]pyridin-4-one | 459 | | 4.08 | 1 | 19, 20 |
| 147 | 2,4-Cl₂—Ph | 2-thienyl | Me | cyclohexyl | 5-cyclohexyl-1-(2,4-dichlorophenyl)-3-methyl-2-(2-thienyl)-1,5,6,7-tetrahydro-4H-pyrrolo[3,2-c]pyridin-4-one | 459 | | 4.10 | 1 | 19, 20 |

TABLE 2-continued

| Entry No. | R¹ | R² | R³ | R⁴ | IUPAC Name | MS m/z (MH+) | TLC Rf (solvent) | HPLC ret. time (LC-MS) | HPLC method | Synthesis Method of Ex. No. |
|---|---|---|---|---|---|---|---|---|---|---|
| 148 | 2,4-Cl₂—Ph | 4-F—Ph | Me | cyclohexyl | 5-cyclohexyl-1-(2,4-dichlorophenyl)-2-(4-fluorophenyl)-3-methyl-1,5,6,7-tetrahydro-4H-pyrrolo[3,2-c]pyridin-4-one | 471 | | 4.17 | 1 | 19, 20 |
| 149 | 2,4-Cl₂—Ph | 4-CF₃—Ph | Me | cyclohexyl | 5-cyclohexyl-1-(2,4-dichlorophenyl)-2-(4-trifluoromethylphenyl)-3-methyl-1,5,6,7-tetrahydro-4H-pyrrolo[3,2-c]pyridin-4-one | 521 | | 4.37 | 1 | 19, 20 |
| 150 | 2,4-Cl₂—Ph | 4-MeO—Ph | Me | cyclohexyl | 5-cyclohexyl-1-(2,4-dichlorophenyl)-2-(4-methoxyphenyl)-3-methyl-1,5,6,7-tetrahydro-4H-pyrrolo[3,2-c]pyridin-4-one | 483 | | 4.08 | 1 | 19, 20 |
| 151 | 2-Me—Ph | H | Me | cyclohexyl | 5-cyclohexyl-3-methyl-1-(2-methylphenyl)-1,5,6,7-tetrahydro-4H-pyrrolo[3,2-c]pyridin-4-one | 323 | 0.54(2:1 Hexane/EtOAc) | 3.51 | 1 | 16, 17 |
| 152 | 2-Me—Ph | Br | Me | cyclohexyl | 2-bromo-5-cyclohexyl-3-methyl-1-(2-methylphenyl)-1,5,6,7-tetrahydro-4H-pyrrolo[3,2-c]pyridin-4-one | 401 | 0.22(5:1 Hexane/EtOAc) | 3.74 | 1 | 18 |
| 153 | 2,6-Cl₂—Ph | 4-Cl—Ph | Me | cyclohexyl | 2(4-chlorophenyl)-5-cyclohexyl-1-(2,6-dichlorophenyl)-3-methyl-1,5,6,7-tetrahydro-4H-pyrrolo[3,2-c]pyridin-4-one | 455 | 0.24(5:1 Hexane/EtOAc | 3.8 | 1 | 19, 20 |
| 154 | 2,4-Cl₂—Ph | 4-Me—Ph | Me | cyclohexyl | 5-cyclohexyl-1-(2,4-dichlorophenyl)-3-methyl-2-(4-methylphenyl)-1,5,6,7-tetrahydro-4H-pyrrolo[3,2-c]pyridin-4-one | 467 | | 4.29 | 1 | 19, 20 |
| 155 | 2,4-Cl₂—Ph | 3-MeO—Ph | Me | cyclohexyl | 5-cyclohexyl-1-(2,4-dichlorophenyl)-3-methyl-2-(3-methoxyphenyl)-1,5,6,7-tetrahydro-4H-pyrrolo[3,2-c]pyridin-4-one | 483 | | 4.10 | 1 | 19, 20 |
| 156 | 2,4-Cl₂—Ph | 3-Me—Ph | Me | cyclohexyl | 5-cyclohexyl-1-(2,4-dichlorophenyl)-3-methyl-2-(3-methylphenyl)-1,5,6,7-tetrahydro-4H-pyrrolo[3,2-c]pyridin-4-one | 467 | | 4.27 | 1 | 19, 20 |
| 157 | 2,4-Cl₂—Ph | Ph | Me | cyclohexyl | 5-cyclohexyl-1-(2,4-dichlorophenyl)-3-methyl-2-phenyl-1,5,6,7-tetrahydro-4H-pyrrolo[3,2-c]pyridin-4-one | 453 | | 4.18 | 1 | 19, 20 |
| 158 | 2,4-Cl₂—Ph | 3-CF₃—Ph | Me | cyclohexyl | 5-cyclohexyl-1-(2,4-dichlorophenyl)-3-methyl-2-(3-trifluoromethylphenyl)-1,5,6,7-tetrahydro-4H-pyrrolo[3,2-c]pyridin-4-one | 521 | | 4.34 | 1 | 19, 20 |
| 159 | 2-Me—Ph | 4-F—Ph | Me | cyclohexyl | 5-cyclohexyl-2-(4-fluorophenyl)-3-methyl-1-(2-methylphenyl)-1,5,6,7-tetrahydro-4H-pyrrolo[3,2-c]pyridin-4-one | 417 | 0.44(1:2 EtOAc/Hexane) | 3.93 | 1 | 19, 20 |

TABLE 2-continued

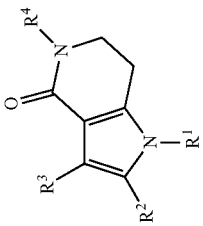

| Entry No. | R¹ | R² | R³ | R⁴ | IUPAC Name | MS m/z (MH+) | TLC Rf (solvent) | HPLC ret. time (LC-MS) | HPLC method | Synthesis Method of Ex. No. |
|---|---|---|---|---|---|---|---|---|---|---|
| 160 | 2-Me—Ph | 4-MeO—Ph | Me | cyclohexyl | 5-cyclohexyl-2-(4-methoxyphenyl)-3-methyl-1-(2-methylphenyl)-1,5,6,7-tetrahydro-4H-pyrrolo[3,2-c]pyridin-4-one | 429 | 0.29(1:2 EtOAc/Hexane) | 3.87 | 1 | 19, 20 |
| 161 | 2-Me—Ph | 4-CF₃—Ph | Me | cyclohexyl | 5-cyclohexyl-2-(4-trifluoromethylphenyl)-3-methyl-1-(2-methylphenyl)-1,5,6,7-tetrahydro-4H-pyrrolo[3,2-c]pyridin-4-one | 467 | 0.46(1:2 EtOAc/Hexane) | 4.18 | 1 | 19, 20 |
| 162 | 2,4-Cl₂—Ph | 3-Cl-4-F—Ph | Me | cyclohexyl | 2-(3-chloro-4-fluorophenyl)-5-cyclohexyl-1-(2,4-dichlorophenyl)-3-methyl-1,5,6,7-tetrahydro-4H-pyrrolo[3,2-c]pyridin-4-one | 505 | 0.43(1:2 EtOAc/Hexane) | 4.38 | 1 | 19, 20 |
| 163 | 2,4-Cl₂—Ph | 3,4-(MeO)₂—Ph | Me | cyclohexyl | 5-cyclohexyl-2-(3,4-dimethoxyphenyl)-3-methyl-1-(2-methylphenyl)-1,5,6,7-tetrahydro-4H-pyrrolo[3,2-c]pyridin-4-one | 513 | 0.18(1:2 EtOAc/Hexane) | 3.91 | 1 | 19, 20 |
| 164 | 2,4-Cl₂—Ph | 3-NH₂—Ph | Me | cyclohexyl | 2-(3-aminophenyl)-5-cyclohexyl-1-(2,4-dichlorophenyl)-3-methyl-1,5,6,7-tetrahydro-4H-pyrrolo[3,2-c]pyridin-4-one | 468 | 0.31(1:1 EtOAc/Hexane) | 3.13 | 1 | 19, 20 |
| 165 | 2,4-Cl₂—Ph | 4-NH₂—Ph | Me | cyclohexyl | 2-(4-aminophenyl)-5-cyclohexyl-1-(2,4-dichlorophenyl)-3-methyl-1,5,6,7-tetrahydro-4H-pyrrolo[3,2-c]pyridin-4-one | 468 | 0.36(1:1 EtOAc/Hexane) | 3.16 | 1 | 19, 20 |
| 166 | 2,4-Cl₂—Ph | 1-benzothien-2-yl | Me | cyclohexyl | 2-(1-benzothien-2-yl)-5-cyclohexyl-1-(2,4-dichlorophenyl)-3-methyl-1,5,6,7-tetrahydro-4H-pyrrolo[3,2-c]pyridin-4-one | 509 | 0.39(1:2 EtOAc/Hexane) | 4.41 | 1 | 19, 20 |
| 167 | 2,4-Cl₂—Ph | 2-furyl | Me | cyclohexyl | 5-cyclohexyl-1-(2,4-dichlorophenyl)-2-(2-furyl)-3-methyl-1,5,6,7-tetrahydro-4H-pyrrolo[3,2-c]pyridin-4-one | 443 | 0.39(1:2 EtOAc/Hexane) | 3.98 | 1 | 19, 20 |
| 168 | 2,4-Cl₂—Ph | 1,3-benzodioxol-5-yl | Me | cyclohexyl | 2-(1,3-benzodioxol-5-yl)-5-cyclohexyl-1-(2,4-dichlorophenyl)-3-methyl-1,5,6,7-tetrahydro-4H-pyrrolo[3,2-c]pyridin-4-one | 497 | 0.32(1:2 EtOAc/Hexane) | 4.10 | 1 | 19, 20 |
| 169 | 2-Cl—Ph | H | Me | cyclohexyl | 1-(2-chlorophenyl)-5-cyclohexyl-3-methyl-1,5,6,7-tetrahydro-4H-pyrrolo[3,2-c]pyridin-4-one | 343 | 0.37(1:2 EtOAc/Hexane) | 3.41 | 1 | 16, 17 |
| 170 | 2,4-Cl₂—Ph | 4-HOOCPh | Me | cyclohexyl | 4-[5-cyclohexyl-1-(2,4-dichlorophenyl)-3-methyl-4-oxo-4,5,6,7-tetrahydro-1H-pyrrolo[3,2-c]pyridin-2-yl]benzoic acid | 497 | 0.11(1:1 EtOAc/Hexane) | 3.90 | 1 | 19, 20 |
| 171 | 2,4-Cl₂—Ph | 3-pyridinyl | Me | cyclohexyl | 5-cyclohexyl-1-(2,4-dichlorophenyl)-3-methyl-2-(3-pyridinyl)-1,5,6,7-tetrahydro-4H-pyrrolo[3,2-c]pyridin-4-one | 454 | 0.08(1:2 EtOAc/Hexane) | 2.93 | 1 | 19, 20 |

TABLE 2-continued

| Entry No. | R¹ | R² | R³ | R⁴ | IUPAC Name | MS m/z (MH+) | TLC Rf (solvent) | HPLC ret. time (LC-MS) | HPLC method | Synthesis Method of Ex. No. |
|---|---|---|---|---|---|---|---|---|---|---|
| 172 | 2-Cl—Ph | 4-MeO—Ph | Me | cyclohexyl | 1-(2-chlorophenyl)-5-cyclohexyl-2-(4-methoxyphenyl)-3-methyl-1,5,6,7-tetrahydro-4H-pyrrolo[3,2-c]pyridin-4-one | 449 | 0.31(1:2 EtOAc/Hexane) | 3.77 | 1 | 19, 20 |
| 173 | 2-Cl—Ph | 4-Cl—Ph | Me | cyclohexyl | 1-(2-chlorophenyl)-2-(4-chlorophenyl)-5-cyclohexyl-3-methyl-1,5,6,7-tetrahydro-4H-pyrrolo[3,2-c]pyridin-4-one | 453 | 0.41(1:2 EtOAc/Hexane) | 4.05 | 1 | 19, 20 |
| 174 | 2-Cl—Ph | 4-MeO—Ph | Me | (S,S)-2-hydro-cyclohexyl | 1-(2-chlorophenyl)-5-[(1S,2S)-2-hydroxycyclohexyl]-2-(4-methoxyphenyl)-3-methyl-1,5,6,7-tetrahydro-4H-pyrrolo[3,2-c]pyridin-4-one | 465 | | 3.23 | 1 | 21 |
| 175 | 2-Cl—Ph | 4-Cl—Ph | Me | (S,S)-2-hydroxy-cyclohexyl | 1-(2-chlorophenyl)-5-[(1S,2S)-2-hydroxycyclohexyl]-3-methyl-1,5,6,7-tetrahydro-4H-pyrrolo[3,2-c]pyridin-4-one | 469 | | 3.37 | 1 | 21 |
| 176 | 2-Cl—Ph | 4-Cl—Ph | Me | 2,4-(MeO)₂-benzyl | 2-(4-chlorophenyl)-1-(2,4-dichlorophenyl)-5-(2,4-dimethoxybenzyl)-3-methyl-1,5,6,7-tetrahydro-4H-pyrrolo[3,2-c]pyridin-4-one | 555 | | 4.68 | 2 | 19, 20 |
| 177 | 2-Cl—Ph | 4-Cl—Ph | Me | 1-piperidinyl | 2-(4-chlorophenyl)-1-(2,4-dichlorophenyl)-3-methyl-5-(1-piperidinyl)-1,5,6,7-tetrahydro-4H-pyrrolo[3,2-c]pyridin-4-one | 490 | | 4.06 | 2 | 19, 20 |
| 178 | 2-Cl-4-(4-Cl—Ph)—Ph | 4-Cl—Ph | Me | 1-piperidinyl | 2-(4-chlorophenyl)-1-(3,4-dichloro-1,1'-biphenyl-4-yl)-3-methyl-5-(1-piperidinyl)-1,5,6,7-tetrahydro-4H-pyrrolo[3,2-c]pyridin-4-one | 566 | | 4.43 | 2 | 19, 20 |
| 179 | 2,4-Cl₂—Ph | H | Me | 1-piperidinyl | 1-(2,4-dichlorophenyl)-3-methyl-5-(1-piperidinyl)-1,5,6,7-tetrahydro-4H-pyrrolo[3,2-c]pyridin-4-one | 378 | | 3.44 | 2 | 16, 17 |
| 180 | 2,4-Cl₂—Ph | H | Me | 2,4-(MeO)₂-benzyl | 1-(2,4-dichlorophenyl)-5-(2,4-dimethoxybenzyl)-3-methyl-1,5,6,7-tetrahydro-4H-pyrrolo[3,2-c]pyridin-4-one | 445 | | 4.02 | 2 | 16, 17 |
| 181 | 2,4-Cl₂—Ph | Br | Me | 2,4-(MeO)₂-benzyl | 2-bromo-1-(2,4-dichlorophenyl)-5-(2,4-dimethoxybenzyl)-3-methyl-1,5,6,7-tetrahydro-4H-pyrrolo[3,2-c]pyridin-4-one | 523 | | 4.32 | 2 | 18 |
| 182 | 2,4-Cl₂—Ph | 4-Cl—Ph | Me | H | 2-(4-chlorophenyl)-1-(2,4-dichlorophenyl)-3-methyl-1,5,6,7-tetrahydro-4H-pyrrolo[3,2-c]pyridin-4-one | 405 | | 3.84 | 2 | 22 |
| 183 | 2,4-Cl₂—Ph | 4-Cl—Ph | Me | 1-piperidinyl | 2-(4-chlorophenyl)-1-(2,4-dichlorophenyl)-3-methyl-5-(1-piperidinyl)-1,5,6,7-tetrahydro-4H-pyrrolo[3,2-c]pyridin-4-one hydrochloride | 490 | | 4.13 | 2 | 19, 20 |

TABLE 2-continued

| Entry No. | R¹ | R² | R³ | R⁴ | IUPAC Name | MS m/z (MH+) | TLC Rf (solvent) | HPLC ret. time (LC-MS) | HPLC method | Synthesis Method of Ex. No. |
|---|---|---|---|---|---|---|---|---|---|---|
| 184 | 2,4-Cl₂—Ph | 4-Cl—Ph | Me | 2-pyridinyl | 2-(4-chlorophenyl)-1-(2,4-dichlorophenyl)-3-methyl-5-(2-pyridinyl)-1,5,6,7-tetrahydro-4H-pyrrolo[3,2-c]pyridin-4-one trifluoroacetate | 482 | | 4.28 | 2 | 23 |
| 185 | 2-Cl—Ph | 4-Cl—Ph | Me | 4-(N-benzyl)-piperidinyl | 5-(1-benzyl-4-piperidinyl)-1-(2-chlorophenyl)-2-(4-chlorophenyl)-3-methyl-1,5,6,7-tetrahydro-4H-pyrrolo[3,2-c]pyridin-4-one hydrochloride | 544 | | 3.01 | 2 | 19, 20 |
| 186 | 2-Cl—Ph | 4-Cl—Ph | Me | 4-piperidinyl | 1-(2-chlorophenyl)-2-(4-chlorophenyl)-3-methyl-5-(4-piperidinyl)-1,5,6,7-tetrahydro-4H-pyrrolo[3,2-c]pyridin-4-one trifluoroacetate | 454 | | 2.74 | 2 | 24 |
| 187 | 2-Cl—Ph | 4-Me—Ph | Me | 4-(N-benzyl)-piperidinyl | 5-(1-benzyl-4-piperidinyl)-1-(2-chlorophenyl)-3-methyl-2-(4-methylphenyl)-1,5,6,7-tetrahydro-4H-pyrrolo[3,2-c]pyridin-4-one hydrochloride | 524 | | 4.44 | 2 | 19, 20 |
| 188 | 2-Cl—Ph | 4-CF₃—Ph | Me | 4-(N-benzyl)-piperidinyl | 5-(1-benzyl-4-piperidinyl)-1-(2-chlorophenyl)-3-methyl-2-(4-trifluoromethylphenyl)-1,5,6,7-tetrahydro-4H-pyrrolo[3,2-c]pyridin-4-one hydrochloride | 578 | | 2.89 | 2 | 19, 20 |
| 189 | 2-Cl—Ph | 4-MeO—Ph | Me | 1-piperidinyl | 1-(2-chlorophenyl)-2-(4-methoxyphenyl)-3-methyl-5-(1-piperidinyl)-1,5,6,7-tetrahydro-4H-pyrrolo[3,2-c]pyridin-4-one hydrochloride | 450 | | 3.33 | 2 | 19, 20 |
| 190 | 2-Me—Ph | 4-MeO—Ph | Me | 1-piperidinyl | 2-(4-methoxyphenyl)-3-methyl-1-(2-methylphenyl)-5-(1-piperidinyl)-1,5,6,7-tetrahydro-4H-pyrrolo[3,2-c]pyridin-4-one hydrochloride | 430 | | 3.29 | 2 | 19, 20 |
| 191 | 2-Cl—Ph | 4-Cl—Ph | Me | H | 1-(2-chlorophenyl)-2-(4-chlorophenyl)-3-methyl-1,5,6,7-tetrahydro-4H-pyrrolo[3,2-c]pyridin-4-one | 371 | | 3.25 | 1 | 22 |
| 192 | 2-Cl—Ph | 4-Cl—Ph | Me | 1-piperidinyl | 1-(2-chlorophenyl)-2-(4-chlorophenyl)-3-methyl-5-(1-piperidinyl)-1,5,6,7-tetrahydro-4H-pyrrolo[3,2-c]pyridin-4-one hydrochloride | 454 | | 3.25 | 2 | 19, 20 |

Evaluation of Biological Activity

Evaluation of Compound's Efficacy on the Reduction of Food Intake (Appetite Suppression) in Lean Overnight Fasted Rats Fasted-Refed Acute Feeding Assay The purpose of this protocol is to determine the effect of a single dose of an unknown compound on food consumption of lean overnight fasted rats. The fasted-refed rat model is frequently used in the field of obesity to identify compounds with potential for anorectic effects. This animal model has been successfully used in the identification and characterization of the efficacy profile of compounds that are or have been used in the management of body weight in obese humans (see, e.g., Balvet et al., Gen. Pharmacol. 13:293–297, 1982; Grignaschi et al., Br. J. Pharmacol. 127:1190–1194, 1999; McTavish and Heel, Drug 43:713–733, 1992; Rowland et al., Life Sci. 36:2295–2300, 1985).

A typical study includes 60–80 male rats (n=10/treatment group) with an average body weight of approximately 280 g. Rats are kept in standard animal rooms under controlled temperature and humidity and a 12/12 light dark cycle. Rats are single-housed in suspended cages with a mesh floor. Water and food are continuously available unless the animals are being fasted for the study.

The vehicle test: The rats are grouped based upon their performance on a vehicle test. The vehicle test is performed between 2 and 7 days before the efficacy test. The rats are fasted overnight during the dark phase (total of approx. 16–18 hrs). The animal is dosed with 0.5 mL deionized water. One hour after dosing, pre-weighed food jars are returned to the animal home cage. The rats are allowed one hour of feeding time. After 1 hour, the spillage is returned to the food jar and the amount of food consumed is determined. The rats are assigned to groups so that the mean and standard error of the mean of 1-hour food consumption are similar between groups.

The efficacy test: The rats are fasted overnight during the dark phase (total of approx. 16–18 hr). The animal is dosed with an assigned treatment (2 mg/ml). One hour after dosing, pre-weighed food jars are returned to the cage. Food intake is recorded 30, 60, 90, 180, and 240 minutes post-food return. At each time point, spillage is returned to the food jar and then the food jars are weighed. The amount of food consumed is determined for each time point. Difference between treatment group is determined using appropriate statistical analysis.

Compounds of this invention were found to be active in this fasted-refed acute feeding assay. For example, when the derivative trans-2-[1-(2-chlorophenyl)-2-(4-chlorophenyl)-1,4,6,7-tetrahydro-5H-pyrrolo[3,2-c]pyridin-5-yl]cyclohexanol hydrochloride (Table 1, entry 18) was dosed at 10 mg/kg p.o., food consumption was reduced (relative to the food consumption observed for the vehicle control group) by 33% to 44% when measured at time points from 30 to 240 minutes. Likewise, when the derivative 1-(2-chlorophenyl)-2-(4-methoxyphenyl)-3-methyl-5-(1-piperidinyl)-1,5,6,7-tetrahydro-4H-pyrrolo[3,2-c]pyridin-4-one hydrochloride (Table 2, entry 189) was dosed at 10 mg/kg p.o., food consumption was reduced (relative to the food consumption observed for the vehicle control group) by 35% to 52% when measured at time points from 30 to 240 minutes.

Evaluation of Compound's Efficacy on the Reduction of Body Weight and Food and Water Consumption in Obese Zucker fa/fa Rats Chronic Feeding Assay The purpose of this protocol is to determine the effect of chronic administration of an unknown compound on body weight and food and water consumption in obese Zucker fa/fa rats. Obese Zucker fa/fa rats are frequently used in the determination of compound efficacy in the reduction of body weight. This animal model has been successfully used in the identification and characterization of the efficacy profile of compounds that are or have been used in the management of body weight in obese humans (see, e.g., Al-Barazanji et al., Obes Res. 8:317–323, 2000; Assimacopoulos-Jeannet et al., Am. J. Physiol. 260(2 Pt 2):R278–283, 1991; Dryden et al., Horm. Metab. Res. 31:363–366, 1999; Edwards and Stevens, Pharmacol. Biochem. Behav. 47:865–872, 1994; Grinker et al., Pharmacol. Biochem. Behav. 12:265–275, 1980).

A typical study includes 60–80 male Zucker fa/fa (n=10/treatment group) with an average body weight of approximately 550 g. Rats are kept in standard animal rooms under controlled temperature and humidity and a 12/12 light dark cycle. Water and food are continuously available. Rats are single-housed in large rat shoeboxes containing grid floor. Animals are adapted to the grid floors and sham-dosed with study vehicle for at least four days before the recording of two-days baseline measurement of body weight and 24-hr food and water consumption. Rats are assigned to one of 6–8 treatment groups based upon their body weight on baseline. The groups are set up so that the mean and standard error of the mean of body weight were similar.

Animals are orally gavaged (2 mL/kg) daily before the dark phase of the LD/cycle for a pre-determined number of days (typically 6–14 days) with their assigned dose/compound. At this time, body weight, food and water consumption are measured. On the final day, animals are euthanized by $CO_2$ inhalation, and the body weight is measured.

The efficacy of compounds of this invention on the reduction or control of body weight are determined by using this chronic feeding assay. For example, when the derivative 1-(2-chlorophenyl)-2-(4-methoxyphenyl)-3-methyl-5-(1-piperidinyl)-1,5,6,7-tetrahydro-4H-pyrrolo[3,2-c]pyridin-4-one hydrochloride (Table 2, entry 189) was dosed once per day at 10 mg/kg p.o., on day 6 of treatment there was no increase in body weight from baseline, whereas an approximately 2% increase in body weight from baseline was observed in the vehicle control group.

Measurement of Brain Exposure

Male obese Zucker fa/fa rats are administered compounds, typically at 10 mg/kg p.o., and then brains are collected at 2 hours post-dosing for determination of brain concentration. Brains are weighed and homogenized with 4 mL 10 mM ammonium acetate buffer (pH 3), and the brain tissue homogenate samples are extracted via protein precipitation with acetonitrile. Samples are vortexed, centrifuged, and analyzed by liquid chromatography utilizing mass spectrometer selective detection (LC/MS/MS) using the heated nebulizer interface. Samples are quantitated using weighted ($1/x^2$) linear internal standard calibration curve.

Compounds of this invention were found to penetrate the brain, resulting in significant brain exposure, by using this assay. For example, when trans-2-[1-(2-chlorophenyl)-2-(4-chlorophenyl)-1,4,6,7-tetrahydro-5H-pyrrolo[3,2-c]pyridin- 5-yl]cyclohexanol hydrochloride (Table 1, entry 18) was dosed at 10 mg/kg p.o., a brain homogenate exposure level of >500 nM was determined.

Demonstration of the various activities of the compounds of the present invention may be accomplished through in vitro, ex vivo, and in vivo assays that are well known in the art. For example, to demonstrate the efficacy of a pharmaceutical agent for the treatment of diabetes and related disorders such as Syndrome X, impaired glucose tolerance, impaired fasting glucose, and hyperinsulinemia or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 14 days. At this point, the animals are bled again by eye or tail vein and blood glucose levels are determined. In each case, glucose levels are measured with a Glucometer Elite XL (Bayer Corporation, Elkhart, Ind.).

Method for Measuring Triglyceride Levels hApoA1 mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 8 days. The animals are then bled again by eye or tail vein, and serum triglyceride levels are determined. In each case, triglyceride levels are measured using a Technicon Axon Autoanalyzer (Bayer Corporation, Tarrytown, N.Y.).

Method for Measuring HDL-Cholesterol Levels

To determine plasma HDL-cholesterol levels, hApoA1 mice are bled and grouped with equivalent mean plasma HDL-cholesterol levels. The mice are orally dosed once daily with vehicle or test compound for 7 days, and then bled again on day 8. Plasma is analyzed for HDL-cholesterol using the Synchron Clinical System (CX4) (Beckman Coulter, Fullerton, Calif.).

Method for Measuring Total Cholesterol, HDL-Cholesterol, Triglycerides, and Glucose Levels In another in vivo assay, obese monkeys are bled, then orally dosed once daily with vehicle or test compound for 4 weeks, and then bled again. Serum is analyzed for total cholesterol, HDL-cholesterol, triglycerides, and glucose using the Synchron Clinical System (CX4) (Beckman Coulter, Fullerton, Calif.). Lipoprotein subclass analysis is performed by NMR spectroscopy as described by Oliver et al., (Proc. Natl. Acad. Sci. USA 98:5306–5311, 2001).

Method for Measuring an Effect on Cardiovascular Parameters

Cardiovascular parameters (e.g., heart rate and blood pressure) are also evaluated. SHR rats are orally dosed once daily with vehicle or test compound for 2 weeks. Blood pressure and heart rate are determined using a tail-cuff method as described by Grinsell et al., (Am. J. Hypertens. 13:370–375, 2000). In monkeys, blood pressure and heart rate are monitored as described by Shen et al., (J. Pharmacol. Exp. Therap. 278:1435–1443, 1996).

In addition, to demonstrate CNS activities of the compounds of the present invention, the following in vivo assays may be used.

Method for Testing Task Learning and Spatial Memory

The Morris Water Maze is routinely used to assess task learning and spatial memory (Jaspers et al., Neurosci. Lett. 117:149–153, 1990; Morris, J. Neurosci. Methods 11:47–60, 1984). In this assay, animals are placed in a water pool which is divided into quadrants. One platform is hidden in one of the quadrants. The animal is placed in the water pool and is expected to locate the hidden platform within a predetermined time. During a number of training trials, the animal learns the location of the platform and escape from the pool. The animal receives multiple trials in this task. Total distance traveled, number of trials to locate platform, latency to find platform, and the swimming path is recorded for each animal. The animal's learning ability is measured by the length of time or number of trials required to find the hidden platform. Memory deficit or improvement is determined by the number of trials or the latency to find the platform at predetermined delay time after acquisition. Leaning and memory may be measured by the number of times that the animal crosses the quadrant where the platform was located during the acquisition phase.

Method for Testing Drug Dependence

Self-administration in animals is a predictor of a compound's abuse potential in humans. Modifications to this procedure may also be used to identify compounds that prevent or block the reinforcing properties of drugs that have abuse potential. A compound that extinguishes the self-administration of a drug may prevent that drug's abuse or its dependence. (Ranaldi et al., Psychopharmacol. 161:442–448, 2002; Campbell et al., Exp. Clin. Psychopharmacol. 8:312–25, 2000). In a self-administration test, animals are placed in the operant chambers containing both an active and inactive lever. Each response on the active lever produces an infusion of either the test compound or a drug known to be self-administered. Presses on the inactive lever have no effect, but are also recorded. Animals are then trained to self-administer compound/drug over a set period of time by having drug access during each daily session. Illumination of the chamber house light signals the beginning of the session and the availability of the compound/drug. When the session ends, the house light is turned off. Initially, a drug infusion occurs with every press of the active lever. Once lever-pressing behavior has been established, the number of presses to produce a drug infusion is increased. After stable compound/drug self-administration is obtained, the effect of a second compound on the drug-reinforced behavior may be evaluated. Administration of this second compound prior to the session can either potentiate, extinguish, or produce no change to the self-administrating behavior. Tests are conducted every two days, and the order of the administration of the test compound doses is controlled.

Pharmaceutical Compositions

Based on the above tests, or other well known assays used to determine the efficacy for treatment of conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered may generally range from about 0.001 mg/kg to about 200 mg/kg, and preferably from about 0.01 mg/kg to about 200 mg/kg body weight per day. A unit dosage may contain from about 0.05 mg to about 1500 mg of active ingredient, and may be administered one or more times per day. The daily dosage for administration by injection, including intravenous, intramuscular, subcutaneous, and parenteral injections, and use of infusion techniques may be from about 0.01 to about 200 mg/kg. The daily rectal dosage regimen may be from 0.01 to 200 mg/kg of total body weight. The transdermal concentration may be that required to maintain a daily dose of from 0.01 to 200 mg/kg.

Of course, the specific initial and continuing dosage regimen for each patient will vary according to the nature and severity of the condition as determined by the attending diagnostician, the activity of the specific compound employed, the age of the patient, the diet of the patient, time of administration, route of administration, rate of excretion of the drug, drug combinations, and the like. The desired mode of treatment and number of doses of a compound of the present invention or a pharmaceutically acceptable salt thereof may be ascertained by those skilled in the art using conventional treatment tests.

The compounds of this invention may be utilized to achieve the desired pharmacological effect by administration to a patient in need thereof in an appropriately formulated pharmaceutical composition. A patient, for the purpose of this invention, is a mammal, including a human, in need of treatment for a particular condition or disease. Therefore, the present invention includes pharmaceutical compositions which are comprised of a pharmaceutically acceptable carrier and a pharmaceutically effective amount of a compound identified by the methods described herein, or a pharmaceutically acceptable salt or ester thereof. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of a compound is that amount which produces a result or exerts an influence on the particular condition being treated. The compounds identified by the methods described herein may be administered with a pharmaceutically-acceptable carrier using any effective conventional dosage unit forms, including, for example, immediate and timed release preparations, orally, parenterally, topically, or the like.

For oral administration, the compounds may be formulated into solid or liquid preparations such as, for example, capsules, pills, tablets, troches, lozenges, melts, powders, solutions, suspensions, or emulsions, and may be prepared according to methods known to the art for the manufacture of pharmaceutical compositions. The solid unit dosage forms may be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose, and cornstarch in combination with binders such as acacia, cornstarch, or gelatin; disintegrating agents intended to assist the break-up and dissolution of the tablet following administration such as potato starch, alginic acid, corn starch, and guar gum; lubricants intended to improve the flow of tablet granulation and to prevent the adhesion of tablet material to the surfaces of the tablet dies and punches, for example, talc, stearic acid, or magnesium, calcium or zinc stearate; dyes; coloring agents; and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and polyethylene alcohols, either with or without the addition of a pharmaceutically acceptable surfactant, suspending agent, or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent, and one or more preservatives. Suitable dispersing or wetting agents and suspending agents are exemplified by those already mentioned above. Additional excipients, for example, those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, and (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil, or coconut oil; or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol, or sucrose. Such formulations may also contain a demulcent, and preservative, flavoring and coloring agents.

The compounds of this invention may also be administered parenterally, that is, subcutaneously, intravenously, intramuscularly, or interperitoneally, as injectable dosages of the compound in a physiologically acceptable diluent with a pharmaceutical carrier which may be a sterile liquid or mixture of liquids such as water, saline, aqueous dextrose and related sugar solutions; an alcohol such as ethanol, isopropanol, or hexadecyl alcohol; glycols such as propylene glycol or polyethylene glycol; glycerol ketals such as 2,2-dimethyl-1,1-dioxolane-4-methanol, ethers such as poly (ethyleneglycol) 400; an oil; a fatty acid; a fatty acid ester or glyceride; or an acetylated fatty acid glyceride with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention may typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono or diglycerides. In addition, fatty acids such as oleic acid may be used in the preparation of injectables.

A composition of the invention may also be administered in the form of suppositories for rectal administration of the drug. These compositions may be prepared by mixing the drug with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, incorporated herein by reference). Such patches may be constructed for continuous, pulsatile, or on demand delivery of pharmaceutical agents.

It may be desirable or necessary to introduce the pharmaceutical composition to the patient via a mechanical delivery device. The construction and use of mechanical delivery devices for the delivery of pharmaceutical agents is well known in the art. For example, direct techniques for administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, incorporated herein by reference.

The compositions of the invention may also contain other conventional pharmaceutically acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

Commonly used pharmaceutical ingredients which may be used as appropriate to formulate the composition for its intended route of administration include: acidifying agents, for example, but are not limited to, acetic acid, citric acid, fumaric acid, hydrochloric acid, nitric acid; and alkalinizing agents such as, but are not limited to, ammonia solution, ammonium carbonate, diethanolamine, monoethanolamine, potassium hydroxide, sodium borate, sodium carbonate, sodium hydroxide, triethanolamine, trolamine.

Other pharmaceutical ingredients include, for example, but are not limited to, adsorbents (e.g., powdered cellulose and activated charcoal); aerosol propellants (e.g., carbon dioxide, $CCl_2F_2$, $F_2ClC—CClF_2$ and $CClF_3$); air displacement agents (e.g., nitrogen and argon); antifungal preservatives (e.g., benzoic acid, butylparaben, ethylparaben, methylparaben, propylparaben, sodium benzoate); antimicrobial preservatives (e.g., benzalkonium chloride, benzethonium chloride, benzyl alcohol, cetylpyridinium chloride, chlorobutanol, phenol, phenylethyl alcohol, phenylmercuric nitrate and thimerosal); antioxidants (e.g., ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite); binding materials (e.g., block polymers, natural and synthetic rubber, polyacrylates, polyurethanes, silicones and styrene-butadiene copolymers); buffering agents (e.g., potassium metaphosphate, potassium phosphate monobasic, sodium acetate, sodium citrate anhydrous and sodium citrate dihydrate); carrying agents (e.g., acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection); chelating agents (e.g., edetate disodium and edetic acid); colorants (e.g., FD&C Red No. 3, FD&C Red No. 20, FD&C Yellow No. 6, FD&C Blue No. 2, D&C Green No. 5, D&C Orange No. 5, D&C Red No. 8, caramel and ferric oxide red); clarifying agents (e.g., bentonite); emulsifying agents (but are not limited to, acacia, cetomacrogol, cetyl alcohol, glyceryl monostearate, lecithin, sorbitan monooleate, polyethylene 50 stearate); encapsulating agents (e.g., gelatin and cellulose acetate phthalate); flavorants (e.g., anise oil, cinnamon oil, cocoa, menthol, orange oil, peppermint oil and vanillin); humectants (e.g., glycerin, propylene glycol and sorbitol); levigating agents (e.g., mineral oil and glycerin); oils (e.g., arachis oil, mineral oil, olive oil, peanut oil, sesame oil and vegetable oil); ointment bases (e.g., lanolin, hydrophilic ointment, polyethylene glycol ointment, petrolatum, hydrophilic petrolatum, white ointment, yellow ointment, and rose water ointment); penetration enhancers (transdermal delivery) (e.g., monohydroxy or polyhydroxy alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas); plasticizers (e.g., diethyl phthalate and glycerin); solvents (e.g., alcohol, corn oil, cottonseed oil, glycerin, isopropyl alcohol, mineral oil, oleic acid, peanut oil, purified water, water for injection, sterile water for injection and sterile water for irrigation); stiffening agents (e.g., cetyl alcohol, cetyl esters wax, microcrystalline wax, paraffin, stearyl alcohol, white wax and yellow wax); suppository bases (e.g., cocoa butter and polyethylene glycols (mixtures)); surfactants (e.g., benzalkonium chloride, nonoxynol 10, oxtoxynol 9, polysorbate 80, sodium lauryl sulfate and sorbitan monopalmitate); suspending agents (e.g., agar, bentonite, carbomers, carboxymethylcellulose sodium, hydroxyethyl cellulose, hydroxypropyl cellulose, hydroxypropyl methylcellulose, kaolin, methylcellulose, tragacanth and veegum); sweetening e.g., aspartame, dextrose, glycerin, mannitol, propylene glycol, saccharin sodium, sorbitol and sucrose); tablet anti-adherents (e.g., magnesium stearate and talc); tablet binders (e.g., acacia, alginic acid, carboxymethylcellulose sodium, compressible sugar, ethylcellulose, gelatin, liquid glucose, methylcellulose, povidone and pregelatinized starch); tablet and capsule diluents (e.g., dibasic calcium phosphate, kaolin, lactose, mannitol, microcrystalline cellulose, powdered cellulose, precipitated calcium carbonate, sodium carbonate, sodium phosphate, sorbitol and starch); tablet coating agents (e.g., liquid glucose, hydroxyethyl cellulose, hydroxypropyl cellulose, hydroxypropyl methylcellulose, methylcellulose, ethylcellulose, cellulose acetate phthalate and shellac); tablet direct compression excipients (e.g., dibasic calcium phosphate); tablet disintegrants (e.g., alginic acid, carboxymethylcellulose calcium, microcrystalline cellulose, polacrillin potassium, sodium alginate, sodium starch glycollate and starch); tablet glidants (e.g., colloidal silica, corn starch and talc); tablet lubricants (e.g., calcium stearate, magnesium stearate, mineral oil, stearic acid and zinc stearate); tablet/capsule opaquants (e.g., titanium dioxide); tablet polishing agents (e.g., carnuba wax and white wax); thickening agents (e.g., beeswax, cetyl alcohol and paraffin); tonicity agents (e.g., dextrose and sodium chloride); viscosity increasing agents (e.g., alginic acid, bentonite, carbomers, carboxymethylcellulose sodium, methylcellulose, povidone, sodium alginate and tragacanth); and wetting agents (e.g., heptadecaethylene oxycetanol, lecithins, polyethylene sorbitol monooleate, polyoxyethylene sorbitol monooleate, and polyoxyethylene stearate).

The compounds identified by the methods described herein may be administered as the sole pharmaceutical agent or in combination with one or more other pharmaceutical agents where the combination causes no unacceptable adverse effects. For example, the compounds of this invention can be combined with known anti-obesity, or with known antidiabetic or other indication agents, and the like, as well as with admixtures and combinations thereof.

The compounds identified by the methods described herein may also be utilized, in free base form or in compositions, in research and diagnostics, or as analytical reference standards, and the like. Therefore, the present invention includes compositions which are comprised of an inert carrier and an effective amount of a compound identified by the methods described herein, or a salt or ester thereof. An inert carrier is any material which does not interact with the compound to be carried and which lends support, means of conveyance, bulk, traceable material, and the like to the compound to be carried. An effective amount of compound is that amount which produces a result or exerts an influence on the particular procedure being performed.

Formulations suitable for subcutaneous, intravenous, intramuscular, and the like; suitable pharmaceutical carriers; and techniques for formulation and administration may be prepared by any of the methods well known in the art (see, e.g., Remington's Pharmaceutical Sciences, Mack Publishing Co., Easton, Pa., 20$^{th}$ edition, 2000)

The following examples are presented to illustrate the invention described herein, but should not be construed as limiting the scope of the invention in any way.

Capsule Formulation

A capsule formula is prepared from:

| Compound of this invention | 40 mg |
|---|---|
| Starch | 109 mg |
| Magnesium stearate | 1 mg |

The components are blended, passed through an appropriate mesh sieve, and filled into hard gelatin capsules.

Tablet Formulation

A tablet is prepared from:

| Compound of this invention | 25 mg |
|---|---|
| Cellulose, microcrystaline | 200 mg |
| Colloidal silicon dioxide | 10 mg |
| Stearic acid | 5.0 mg |

The ingredients are mixed and compressed to form tablets. Appropriate aqueous and non-aqueous coatings may be applied to increase palatability, improve elegance and stability or delay absorption.

Sterile IV Solution

A 5 mg/ml solution of the desired compound of this invention is made using sterile, injectable water, and the pH is adjusted if necessary. The solution is diluted for administration to 1–2 mg/ml with sterile 5% dextrose and is administered as an IV infusion over 60 minutes.

Intramuscular Suspension

The following intramuscular suspension is prepared:

| Compound of this invention | 50 mg/ml |
|---|---|
| Sodium carboxymethylcellulose | 5 mg/ml |
| TWEEN 80 | 4 mg/ml |
| Sodium chloride | 9 mg/ml |
| Benzyl alcohol | 9 mg/ml |

The suspension is administered intramuscularly.

Hard Shell Capsules

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

What is claimed is:

1. A compound of Formula (I)

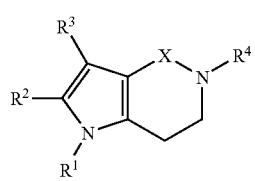

(I)

wherein
- $R^1$ is phenyl optionally substituted with one or more halogen, $(C_1-C_6)$alkyl, $(C_1-C_6)$alkoxy, $(C_1-C_6)$alkylthio, trifluoromethyl, trifluoromethoxy, carboxyl, amino, cyano, nitro, $(C_1-C_6)$alkyl-carbonyl-amino, $(C_1-C_6)$alkyl-amino-carbonyl-amino, or phenyl optionally substituted with one or more halogen;
- $R^2$ is a hydrogen,
  halogen,
  $(C_1-C_9)$alkyl optionally substituted with $(C_1-C_6)$alkoxy, trifluoromethyl, or with one or more fluorine,
  phenyl optionally substituted with one or more halogen, $(C_1-C_6)$alkyl, $(C_2-C_8)$alkenyl, $(C_2-C_8)$alkynyl, $(C_1-C_6)$alkoxy, $(C_1-C_6)$alkyl-thio, trifluoromethyl, trifluoromethoxy, carboxyl, amino, cyano, nitro, $(C_1-C_6)$alkyl-carbonyl-amino, $(C_1-C_6)$alkyl-amino-carbonyl-amino, or phenyl,
  or
  a 5- to 10-membered aromatic monocyclic or bicyclic heterocyclic radical optionally substituted with one or more halogen, $(C_1-C_6)$alkyl, $(C_1-C_6)$alkoxy, trifluoromethyl, trifluoromethoxy, cyano, or nitro;
- $R^3$ is hydrogen, $(C_1-C_6)$alkyl, or benzyl;
- X is —C(=O)—;
- $R^4$ is
  hydrogen,
  $(C_1-C_9)$alkyl optionally substituted with one or more hydroxy, benzyloxy, $(C_1-C_6)$alkoxy, trifluoromethyl, cyano, or fluorine,
  benzyl or phenyl, optionally substituted on the phenyl ring with one or more $(C_1-C_6)$alkyl, hydroxy, $(C_1-C_6)$alkoxy, trifluoromethyl, cyano, nitro, or halogen,
  piperidin-4-yl, piperidin-3-yl, or pyrrolidin-3-yl, each of which may be optionally substituted on the nitrogen atom of the piperidine or pyrrolidine ring with $(C_1-C_6)$alkyl, $(C_1-C_6)$hydroxyalkyl, benzyl, or phenyl, in which the benzyl or phenyl group may optionally be substituted on the phenyl ring with one or more halogen, $(C_1-C_6)$alkyl, $(C_1-C_6)$alkoxy, or trifluoromethyl,
  —$NR^5R^6$ in which $R^5$ and $R^6$, taken together with the nitrogen atom to which they are attached, form a 5- to 10-membered saturated or unsaturated heterocyclic radical which is optionally substituted with one or more $(C_1-C_6)$alkyl, $(C_1-C_6)$alkoxy, hydroxy-substituted $(C_1-C_3)$alkyl, $(C_1-C_3)$alkoxy-substituted $(C_1-C_3)$alkyl, benzyl, phenyl, hydroxy, or fluorine, or
  a 5- to 10-membered aromatic monocyclic or bicyclic heterocyclic radical optionally substituted with one or more halogen, $(C_1-C_6)$alkyl, $(C_1-C_6)$alkoxy, trifluoromethyl, cyano, or nitro;

and pharmaceutical salts and esters thereof.

2. The compound of claim 1, wherein
- $R^1$ is phenyl optionally substituted with one or more halogen or $(C_1-C_6)$alkyl;
- $R^2$ is hydrogen, halogen, or a phenyl optionally substituted with one or more halogen, $(C_1-C_6)$alkyl, $(C_1-C_6)$alkoxy, trifluoromethyl, trifluoromethoxy, carboxyl, or amino;
- $R^3$ is hydrogen or $(C_1-C_6)$alkyl;
- X is —(=O)—;
- $R^4$ is
  hydrogen,
  $(C_1-C_9)$alkyl optionally substituted with one or more hydroxy, benzyloxy, $(C_1-C_6)$alkoxy, trifluoromethyl, cyano, or fluorine,
  benzyl or phenyl, optionally substituted on the phenyl ring with one or more $(C_1-C_6)$alkyl, hydroxy, $(C_1-C_6)$alkoxy, trifluoromethyl, cyano, nitro, or halogen,
  piperidin-4-yl, piperidin-3-yl, or pyrrolidin-3-yl, each of which may be optionally substituted on the nitrogen atom of the piperidine or pyrrolidine ring with $(C_1-C_6)$alkyl, $(C_1-C_6)$hydroxyalkyl, benzyl, or phenyl, in which the benzyl or phenyl group may optionally be substituted on the phenyl ring with one or more halogen, $(C_1-C_6)$alkyl, $(C_1-C_6)$alkoxy, or trifluoromethyl,
  —$NR^5R^6$ in which $R^5$ and $R^6$, taken together with the nitrogen atom to which they are attached, form a 5- to 10-membered saturated or unsaturated heterocyclic radical which is optionally substituted with one or more $(C_1-C_6)$alkyl, $(C_1-C_6)$alkoxy, hydroxy-substituted (C$_1$–C$_3$)alkyl, (C$_1$–C$_3$)alkoxy-substituted (C$_1$–C$_3$)alkyl, benzyl, phenyl, hydroxy, or fluorine,
or
  a 5- to 10-membered aromatic monocyclic or bicyclic heterocyclic radical optionally substituted with one or more halogen, (C$_1$–C$_6$)alkyl, (C$_1$–C$_6$)alkoxy, trifluoromethyl, cyano, or nitro;

and pharmaceutical salts and esters thereof.

3. The compound of claim 2, wherein
R$^1$ is phenyl optionally substituted with one or more halogen or (C$_1$–C$_6$)alkyl;
R$^2$ is hydrogen, halogen, or a phenyl optionally substituted with one or more halogen, (C$_1$–C$_6$)alkyl, (C$_1$–C$_6$)alkoxy, trifluoromethyl, trifluoromethoxy, carboxyl, or amino;
R$^3$ is hydrogen or (C$_1$–C$_6$)alkyl;
X is —C(=O)—;
R$^4$ is
  hydrogen,
  cyclohexyl optionally substituted with one or more hydroxy, benzyloxy, (C$_1$–C$_6$)alkoxy, trifluoromethyl, cyano, or fluorine,
  benzyl, optionally substituted on the phenyl ring with one or more (C$_1$–C$_6$)alkyl, hydroxy, (C$_1$–C$_6$)alkoxy, trifluoromethyl, cyano, nitro, or halogen,
  piperidin-4-yl, optionally substituted on the nitrogen atom of the piperidine ring with (C$_1$–C$_6$)alkyl, (C$_1$–C$_6$)hydroxyalkyl, benzyl, or phenyl, in which the benzyl or phenyl group may optionally be substituted on the phenyl ring with one or more halogen, (C$_1$–C$_6$)alkyl, (C$_1$–C$_6$)alkoxy, or trifluoromethyl,
  piperidin-1-yl, pyrrolidin-1-yl, or azepan-1-yl, optionally substituted with one or more (C$_1$–C$_6$)alkyl, (C$_1$–C$_6$)alkoxy, hydroxy-substituted (C$_1$–C$_3$)alkyl, (C$_1$–C$_3$)alkoxy-substituted (C$_1$–C$_3$)alkyl, benzyl, phenyl, hydroxy, or fluorine,
or
  2-pyridinyl or 4-pyridinyl, optionally substituted with one or more (C$_1$–C$_6$)alkyl, (C$_1$–C$_6$)alkoxy, trifluoromethyl, or cyano;

and pharmaceutical salts and esters thereof.

4. The compound of claim 3, wherein
R$^1$ is phenyl optionally substituted with one or more halogen or (C$_1$–C$_6$)alkyl;
R$^2$ is hydrogen, halogen, or a phenyl optionally substituted with one or more halogen, (C$_1$–C$_6$)alkyl, (C$_1$–C$_6$)alkoxy, trifluoromethyl, trifluoromethoxy, carboxyl, or amino;
R$^3$ is hydrogen or (C$_1$–C$_6$)alkyl;
X is —C(=O)—;
R$^4$ is
  hydrogen,
  cyclohexyl optionally substituted with one or more hydroxy, (C$_1$–C$_6$)alkoxy, or fluorine,
  benzyl, optionally substituted on the phenyl ring with one or more (C$_1$–C$_6$)alkyl, hydroxy, (C$_1$–C$_6$)alkoxy, trifluoromethyl, cyano, or halogen,
  piperidin-4-yl, optionally substituted on the nitrogen atom of the piperidine ring with benzyl, in which the phenyl ring of the benzyl group may optionally be substituted with one or more halogen, (C$_1$–C$_6$)alkyl, (C$_1$–C$_6$)alkoxy, or trifluoromethyl,
  piperidin-1-yl, pyrrolidin-1-yl, or azepan-1-yl, optionally substituted with one or more (C$_1$–C$_6$)alkyl, (C$_1$–C$_6$)alkoxy, hydroxy-substituted (C$_1$–C$_3$)alkyl, hydroxy, or fluorine,
or
  2-pyridinyl or 4-pyridinyl, optionally substituted with one or more (C$_1$–C$_6$)alkyl;

and pharmaceutical salts and esters thereof.

5. The compound of claim 4, wherein
R$^1$ is phenyl optionally substituted with one or more halogen or (C$_1$–C$_6$)alkyl;
R$^2$ is hydrogen, halogen, or a phenyl optionally substituted with one or more halogen, (C$_1$–C$_6$)alkyl, (C$_1$–C$_6$)alkoxy, or trifluoromethyl;
R$^3$ is hydrogen or (C$_1$–C$_6$)alkyl;
X is —C(=O)—;
R$^4$ is
  hydrogen,
  cyclohexyl optionally substituted with one or more hydroxy,
  benzyl, optionally substituted on the phenyl ring with one or more halogen,
  piperidin-4-yl, optionally substituted on the nitrogen atom of the piperidine ring with benzyl, in which the phenyl ring of the benzyl group may optionally be substituted with one or more halogen,
  piperidin-1-yl, pyrrolidin-1-yl, or azepan-1-yl, optionally substituted with one or more (C$_1$–C$_6$)alkyl,
or
  2-pyridinyl, optionally substituted with one or more (C$_1$–C$_6$)alkyl;

and pharmaceutical salts and esters thereof.

6. The compound of claim 5, wherein
R$^1$ is phenyl optionally substituted with one or more halogen or (C$_1$–C$_6$)alkyl;
R$^2$ is hydrogen, halogen, or a phenyl optionally substituted with one or more halogen, (C$_1$–C$_6$)alkyl, (C$_1$–C$_6$)alkoxy, or trifluoromethyl;
R$^3$ is hydrogen or (C$_1$–C$_6$)alkyl;
X is —C(=O)—;
R$^4$ is
  hydrogen,
  cyclohexyl optionally substituted at the 2-position with hydroxy,
  benzyl, optionally substituted on the phenyl ring with one or more halogen,
  piperidin-4-yl, optionally substituted on the nitrogen atom of the piperidine ring with benzyl,
  piperidin-1-yl,
or
  2-pyridinyl;

and pharmaceutical salts and esters thereof.

7. The compound of claim 1 selected from the group consisting of:
  1-(2-chlorophenyl)-5-cyclohexyl-2-(4-methoxyphenyl)-3-methyl-1,5,6,7-tetrahydro-4H-pyrrolo[3,2-c]pyridin-4-one;
  1-(2-chlorophenyl)-2-(4-methoxyphenyl)-3-methyl-5-(1-piperidinyl)-1,5,6,7-tetrahydro-4H-pyrrolo[3,2-c]pyridin-4-one hydrochloride;
  1-2-chlorophenyl)-2-4-chlorophenyl)-5-[(1S,2S)-2-hydroxycyclohexyl]-3-methyl-1,5,6,7-tetrahydro-4H-pyrrolo[3,2-c]pyridin-4-one.

8. A pharmaceutical composition comprising an effective amount of a compound of claim 1, or a pharmaceutically acceptable salt or ester thereof, in combination with a pharmaceutically acceptable carrier.

9. A pharmaceutical composition comprising an effective amount of a compound of claim 7, or a pharmaceutically acceptable salt or ester thereof, in combination with a pharmaceutically acceptable carrier.

10. A pharmaceutical composition comprising an effective amount of a compound of claim 1, or a pharmaceutically acceptable salt or ester thereof, in combination with a pharmaceutically acceptable carrier and one or more hypoglycemic agents.

11. The pharmaceutical composition of claim 10, wherein said hypoglycemic agent is selected from the group consisting of insulin, biguanidines, sulfonylureas, insulin secretagogues, α-glycosidase inhibitors, and $\beta_3$-adrenoreceptor agonists.

12. A pharmaceutical composition comprising an effective amount of a compound of claim 7, or a pharmaceutically acceptable salt or ester thereof, in combination with a pharmaceutically acceptable carrier and one or more hypoglycemic agents.

13. The pharmaceutical composition of claim 12, wherein said hypoglycemic agent is selected from the group consisting of insulin, biguanidines, sulfonylureas, insulin secretagogues, α-glycosidase inhibitors, and $\beta_3$-adrenoreceptor agonists.

14. A pharmaceutical composition comprising an effective amount of a compound of claim 1, or a pharmaceutically acceptable salt or ester thereof, in combination with a pharmaceutically acceptable carrier and one or more agents selected from the group consisting of HMG CoA reductase inhibitor, bile acid binding agent, fibric acid derivative, and agent that regulates hypertension.

15. A pharmaceutical composition comprising an effective amount of a compound of claim 7, or a pharmaceutically acceptable salt or ester thereof, in combination with a pharmaceutically acceptable carrier and one or more agents selected from the group consisting of HMG CoA reductase inhibitor, bile acid binding agent, fibric acid derivative, and agent that regulates hypertension.

16. A composition comprising an effective amount of a compound of claim 1, or a salt or ester thereof, in combination with an inert carrier.

17. A composition comprising an effective amount of a compound of claim 7, or a salt or ester thereof, in combination with an inert carrier.

18. A method of treating obesity and obesity-related disorders comprising the step of administering to a patient in need thereof a pharmaceutically effective amount of a compound of claim 1.

19. The method of claim 18, wherein said obesity-related disorders include dyslipidemia, hypertriglyceridemia, hypertension, diabetes, Syndrome X, atherosclerotic disease, cardiovascular disease, cerebrovascular disease, peripheral vessel disease, cholesterol gallstones, cancer, menstrual abnormalities, infertility, polycystic ovaries, osteoarthritis, and sleep apnea.

20. A method of treating obesity and obesity-related disorders comprising the step of administering to a patient in need thereof a pharmaceutically effective amount of a compound of claim 7.

21. The method of claim 20, wherein said obesity-related disorders include dyslipidemia, hypertriglyceridemia, hypertension, diabetes, Syndrome X, atherosclerotic disease, cardiovascular disease, cerebrovascular disease, peripheral vessel disease, cholesterol gallstones, cancer, menstrual abnormalities, infertility, polycystic ovaries, osteoarthritis, and sleep apnea.

22. A method of regulating appetite and food intake comprising the step of administering to a patient in need thereof a pharmaceutically effective amount of a compound of claim 1.

23. A method of regulating appetite and food intake comprising the step of administering to a patient in need thereof a pharmaceutically effective amount of a compound of claim 7.

24. A method of treating obesity and obesity-related disorders comprising the step of administering to a patient in need thereof a pharmaceutically effective amount of a compound of claim 1 in combination with one or more hypoglycemic agents.

25. A method of treating obesity and obesity-related disorders comprising the step of administering to a patient in need thereof a pharmaceutically effective amount of a compound of claim 7 in combination with one or more hypoglycemic agents.

26. A method of treating obesity and obesity-related disorders comprising the step of administering to a patient in need thereof a pharmaceutically effective amount of a compound of claim 1 in combination with one or more agents selected from the group consisting of HMG CoA reductase inhibitor, bile acid binding agent, fibric acid derivative, and agent that regulates hypertension.

27. A method of treating obesity and obesity-related disorders comprising the step of administering to a patient in need thereof a pharmaceutically effective amount of a compound of claim 7 in combination with one or more agents selected from the group consisting of HMG CoA reductase inhibitor, bile acid binding agent, fibric acid derivative, and agent that regulates hypertension.

\* \* \* \* \*